(12) United States Patent
You et al.

(10) Patent No.: US 11,504,385 B2
(45) Date of Patent: Nov. 22, 2022

US011504385B2

(54) PROTEOLYSIS TARGETING CHIMERIC MOLECULE, PREPARATION METHOD, AND APPLICATION

(71) Applicant: CHINA PHARMACEUTICAL UNIVERSITY, Nanjing (CN)

(72) Inventors: Qidong You, Nanjing (CN); Zhengyu Jiang, Nanjing (CN); Yan Wang, Nanjing (CN); Yuhui Jin, Nanjing (CN); Mengchen Lu, Nanjing (CN); Xiaoli Xu, Nanjing (CN); Xiaoke Guo, Nanjing (CN)

(73) Assignee: CHINA PHARMACEUTICAL UNIVERSITY, Nanjing (CN)

( * ) Notice: Subject to any disclaimer, the term of this patent is extended or adjusted under 35 U.S.C. 154(b) by 0 days.

(21) Appl. No.: 15/734,960

(22) PCT Filed: Sep. 4, 2019

(86) PCT No.: PCT/CN2019/104300
§ 371 (c)(1),
(2) Date: Dec. 3, 2020

(87) PCT Pub. No.: WO2020/151229
PCT Pub. Date: Jul. 30, 2020

(65) Prior Publication Data
US 2021/0338695 A1 Nov. 4, 2021

(30) Foreign Application Priority Data
Jan. 26, 2019 (CN) .......................... 201910076670.4

(51) Int. Cl.
*A61K 31/655* (2006.01)
*A61K 47/55* (2017.01)
*A61K 47/54* (2017.01)
*A61P 35/02* (2006.01)
*A61K 31/506* (2006.01)
*A61K 41/00* (2020.01)

(52) U.S. Cl.
CPC .......... *A61K 31/655* (2013.01); *A61K 31/506* (2013.01); *A61K 41/0023* (2013.01); *A61K 47/54* (2017.08); *A61K 47/55* (2017.08); *A61P 35/02* (2018.01)

(58) Field of Classification Search
CPC ...................................................... A61K 31/655
USPC ........................................................ 514/150
See application file for complete search history.

(56) References Cited

PUBLICATIONS

Jin, J. Med. Chem. 2020, 63, 4644-4654.*

* cited by examiner

*Primary Examiner* — Nizal S Chandrakumar
(74) *Attorney, Agent, or Firm* — CBM Patent Consulting, LLC

(57) ABSTRACT

It discloses a proteolysis targeting chimeric molecule, a preparation method and an application thereof. The proteolysis targeting chimeric molecule provided by the disclosure can inhibit the expression of BCR-ABL and/or CRBN protein in BCR-ABL and/or CRBN positive leukemia K562 cells to varying degrees, and thus can be used to prepare drugs for treating BCR-ABL and/or CRBN positive leukemia, wherein the proteolysis targeting chimeric molecule with n=3 has excellent photo-isomerization activity, and can be used in preparation of the reagents or drugs for light-regulated degradation of BCR-ABL and/or CRBN protein. The disclosure also provides a method for synthesizing the series of proteolysis targeting chimeric molecules.

5 Claims, 11 Drawing Sheets

Specification includes a Sequence Listing.

n=1, 2C;  n=2, 3C;
n=3, 4C;  n=4, 5C.
n=5, 6C;

D

PROTEOLYSIS TARGETING CHIMERIC MOLECULE, PREPARATION METHOD, AND APPLICATION

TECHNICAL FIELD

The disclosure belongs to the field of chemistry, and particularly relates to a proteolysis targeting chimeric molecule, a preparation method and an application thereof.

BACKGROUND ART

Proteolysis targeting chimera (PROTAC) is an emerging technology. This technology can use a ubiquitin-proteasome system to induce ubiquitination degradation of a certain protein by recruiting an E3 ubiquitin ligase of a specific protein, thereby regulating the concentration of the protein. Compared with traditional small molecule inhibitors, PROTAC technology can more effectively act on nonmedicinal proteins.

Clinical studies have shown that BCR-ABL fusion protein is universally present in chronic myeloid leukemia (CML) cases. Also, ABL and BCR-ABL proteins are two of the earliest targets used in PROTAC research. In 2016, the CREWS research group took the lead in using a PROTAC strategy to successfully down-regulate the expression level of the BCR-ABL fusion protein in K562 leukemia cells. The PROTAC small molecule they designed can simultaneously degrade BCR-ABL and ABL proteins at low concentrations.

However, related studies have shown that ABL is involved in response of growth factors and cytokines, and is also related to multiple signaling pathways such as cell adhesion, DNA damage, and oxidative stress. ABL is activated to stimulate cell proliferation or differentiation, survival or death, and withdrawal or migration. Knockout of ABL gene can cause abnormal cell cycle function.

But, what is the way to regulate PROTAC molecules to avoid excessive degradation of ABL protein? A technical problem needs to be solved urgently, namely how to regulate the degradation process of the target protein mediated by PROTAC molecules.

SUMMARY OF THE DISCLOSURE

The disclosure aims to overcome the shortcomings of the prior art and provide an adjustable PROTAC molecule to down-regulate the expression levels of BCR-ABL and ABL proteins in K562 leukemia cells by using a PROTAC strategy reversibly, quickly and easily. At the same time, the disclosure also aims to provide a feasible method for synthesizing and preparing the PROTAC molecule.

The above objectives of the disclosure are achieved through the following technical solutions:

A proteolysis targeting chimeric molecule, including the following chemical structural formula:

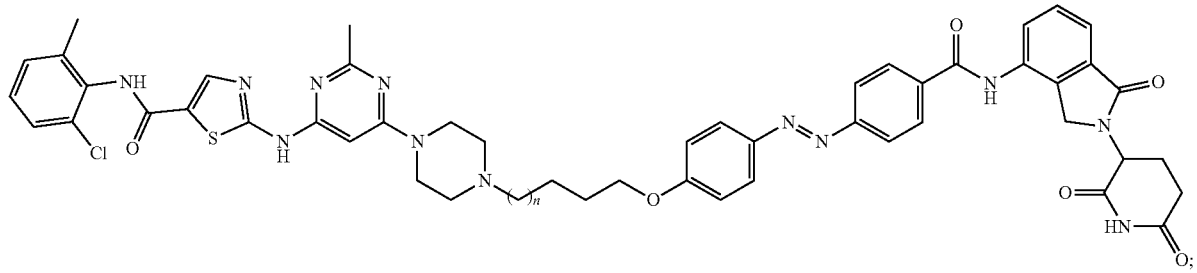

wherein n is any natural number in a range of 1-5.
Preferably, n=3.
A synthesis method of the above proteolysis targeting chimeric molecule, including the following synthesis route:

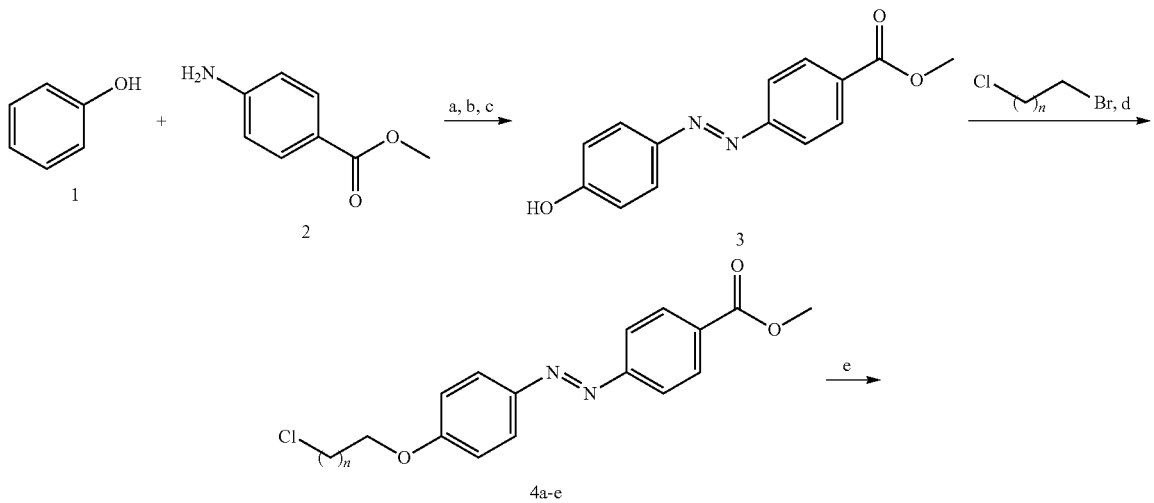

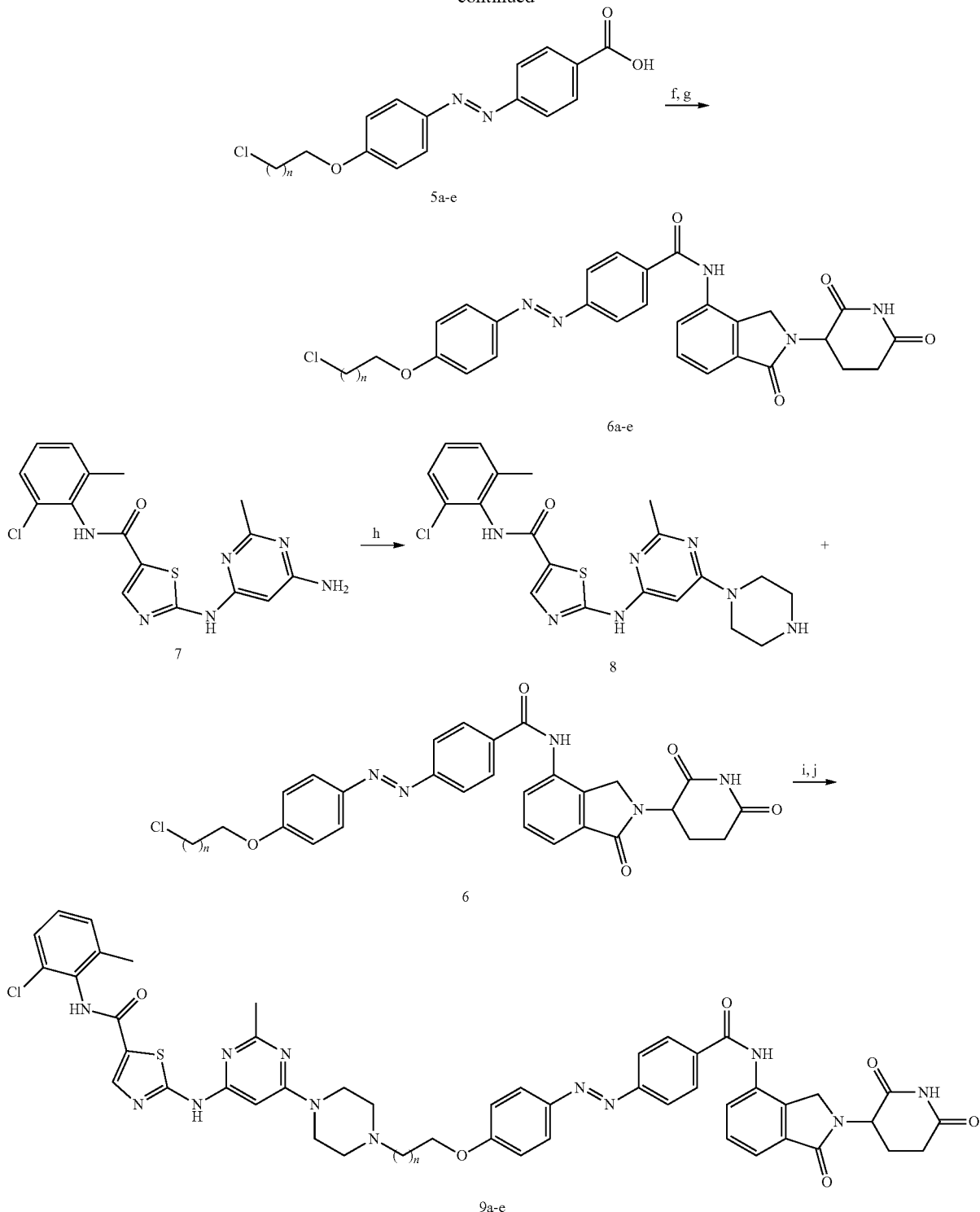
4a, 5a, 6a, 9a: n = 1
4b, 5b, 6b, 9b: n = 2
4c, 5c, 6c, 9c: n = 3
4d, 5d, 6d, 9d: n = 4
4e, 5e, 6e, 9e: n = 5
Reagents and conditions: a) HCl, NaNO$_2$/H$_2$O, 1 h; b) Cs$_2$CO$_3$, H$_2$O, rt, 3 h; c) AcOH, H$_2$O, pH = 4; d) K$_2$CO$_3$, DMF; e) LiOH, THF:H$_2$O = 1:1, r.t., overnight; f) (COCl)$_2$, DMF(cat), DCM; g) Lenalidomide, DIEA, THF, rt., 8 h; h) Piperazine, DIEA, Dioxane, reflux, 24 h; i) NaI, Acetone, reflux, 24 h; j) DIEA, DMF, 16 h;
wherein n is any natural number in a range of 1-5.

An application of the above proteolysis targeting chimeric molecule in preparation of drugs for treating BCR-ABL and/or CRBN positive leukemia is provided.

An application of the proteolysis targeting chimeric molecule with n=3 in preparation of reagents or drugs for light-regulated degradation of BCR-ABL and/or CRBN protein is provided.

Beneficial Effects:

The proteolysis targeting chimeric molecule provided by the disclosure can inhibit the expression of BCR-ABL and/or CRBN protein in BCR-ABL and/or CRBN positive leukemia K562 cells to varying degrees, and thus can be used to prepare drugs for treating BCR-ABL and/or CRBN positive leukemia, wherein the proteolysis targeting chimeric molecule with n=3 has excellent photo-isomerization activity, and can be used in preparation of the reagents or drugs for light-regulated degradation of BCR-ABL and/or CRBN protein. The disclosure also provides a method for synthesizing the series of proteolysis targeting chimeric molecules.

DETAILED DESCRIPTION OF THE DISCLOSURE

Figure 1:
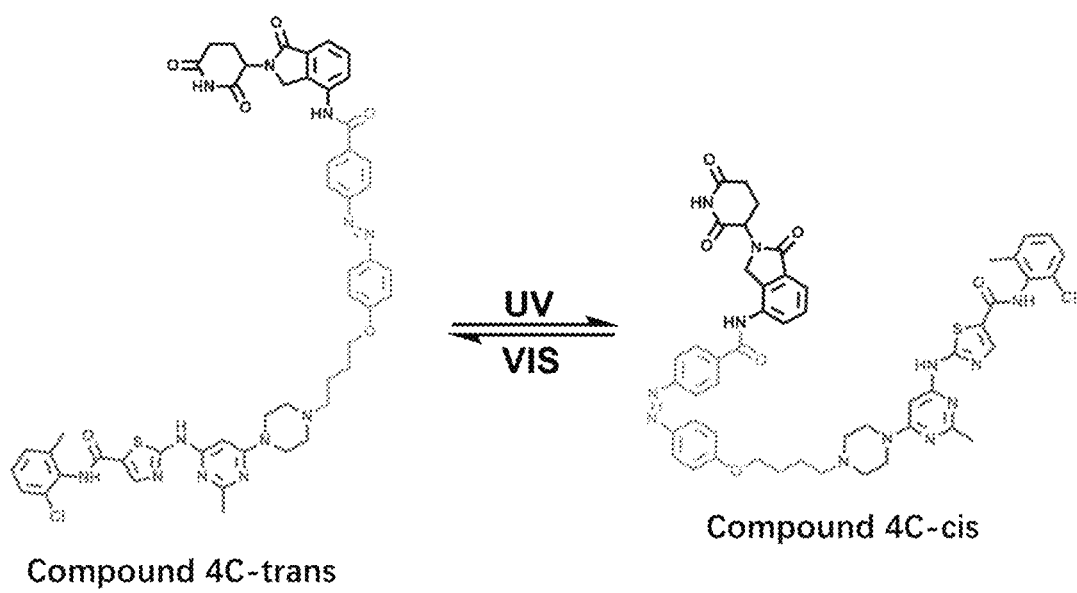
FIG. 1 is a schematic diagram of photo-isomerization of a compound 4C.

The following describes the essential content of the disclosure in detail with reference to the drawings and examples, but the protection scope of the disclosure is not limited thereto. In the examples, the room temperature or the abbreviation rt representing room temperature all refer to normal temperature.

Example 1: Synthesis and Structure Confirmation of PROTAC Molecule

Synthesis Route Map:

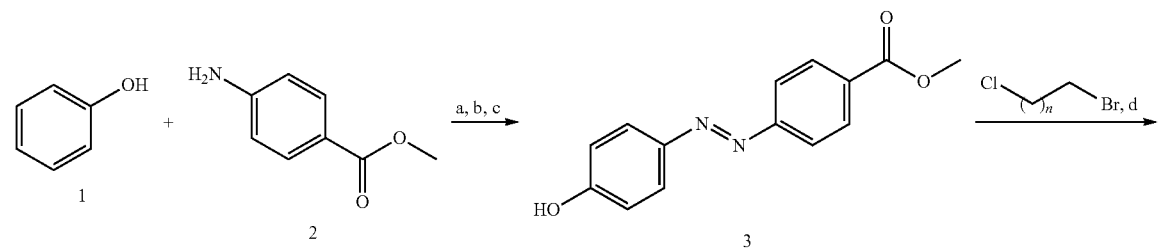

-continued
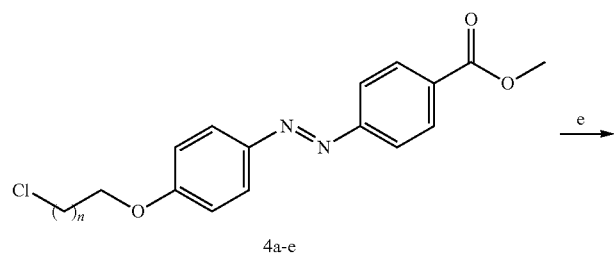
4a-e
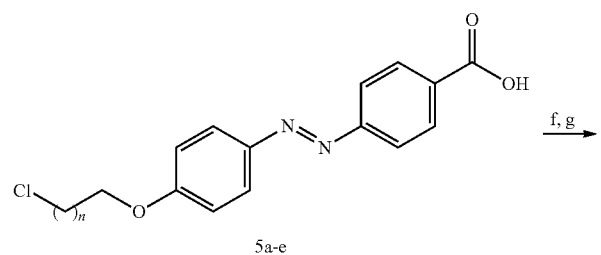
5a-e
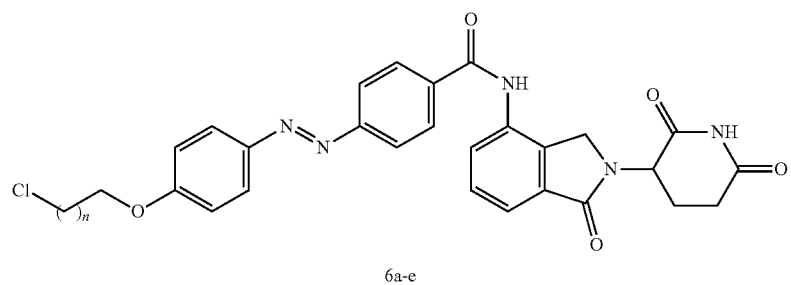
6a-e
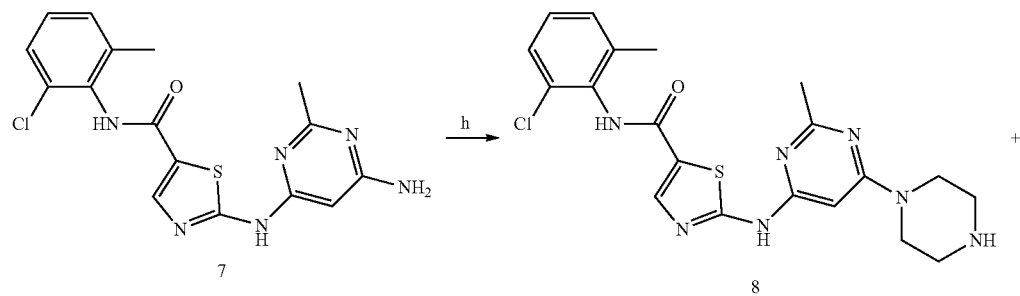
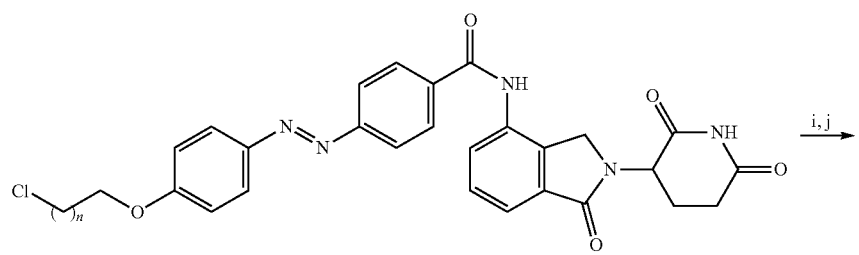
6

-continued

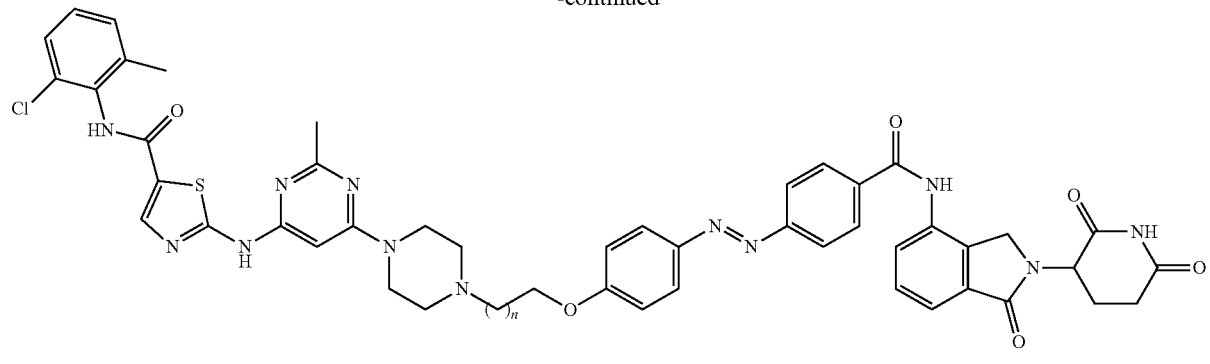

9a-e 4a, 5a, 6a, 9a: n = 1
4b, 5b, 6b, 9b: n = 2
4c, 5c, 6c, 9c: n = 3
4d, 5d, 6d, 9d: n = 4
4e, 5e, 6e, 9e: n = 5

Reagents and conditions: a) HCl, NaNO$_2$/H$_2$O, 1 h; b) Cs$_2$CO$_3$, H$_2$O, rt, 3 h; c) AcOH, H$_2$O, pH = 4; d) K$_2$CO$_3$, DMF; e) LiOH, THF:H$_2$O = 1:1, r.t., overnight; f) (COCl)$_2$, DMF(cat), DCM; g) Lenalidomide, DIEA, THF, rt., 8 h; h) Piperazine, DIEA, Dioxane, reflux, 24 h; i) NaI, Acetone, reflux, 24 h; j) DIEA, DMF, 16 h (E)-4-((4-hydroxyphenyl)diazenyl)methyl benzoate (3)

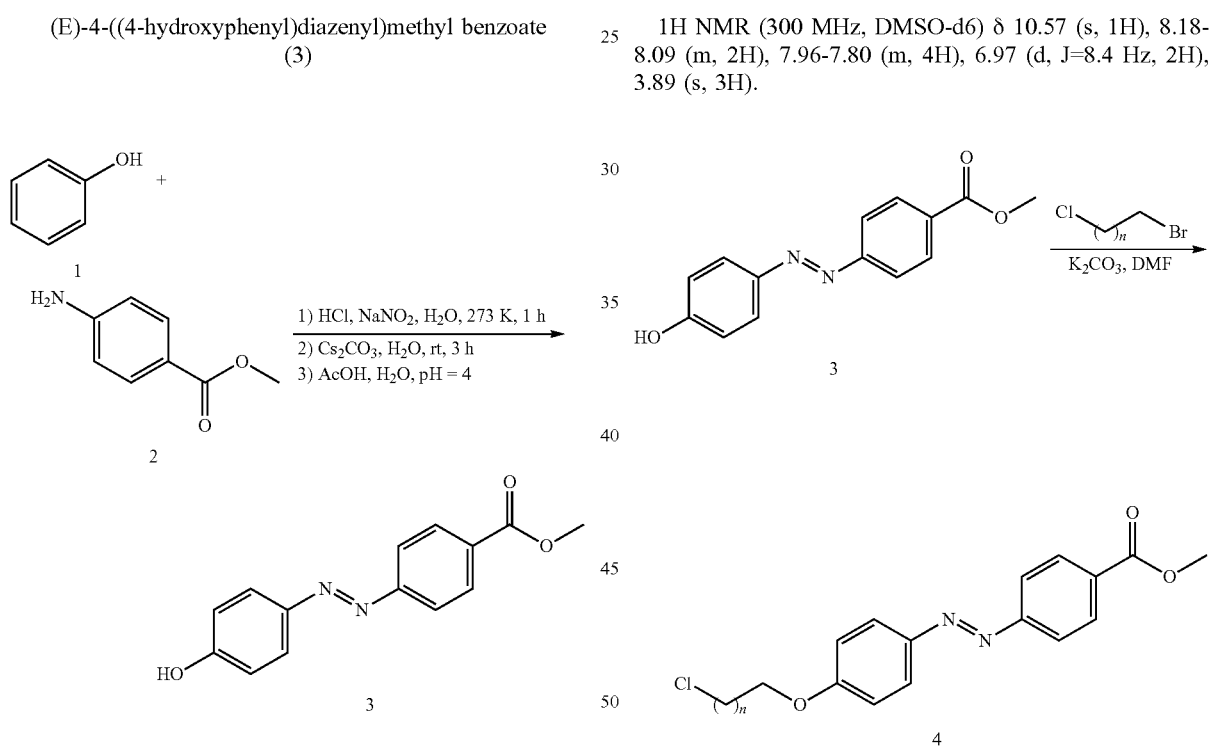

Compound 2 (11.54 g, 76.1 mmol) was dissolved in water (135 ml), HCl (15.8 ml, 190 mmol) was added, and the reaction solution was cooled to 5° C. under ice bath. A pre-cooled aqueous solution (35 ml) of sodium nitrite (5.03 g, 79.8 mmol) was slowly added dropwise to the reaction solution, and the reaction solution was stirred at 5° C. for 1 hour. An aqueous solution (120 ml) of phenol (1) (7.52 g, 79.9 mmol) and K$_2$CO$_3$ (15.0 g, 108.5 mmol) was added dropwise to the reaction solution (within 10 min), and the reaction solution was stirred at room temperature for 3 hours. The pH was adjusted to 4 with dilute acetic acid, and a large amount of brown-yellow solid precipitated. After suction filtration, the filter cake was washed sequentially with water and methanol to obtain a brown solid 3 (15.65 g, 80.3%).

1H NMR (300 MHz, DMSO-d6) δ 10.57 (s, 1H), 8.18-8.09 (m, 2H), 7.96-7.80 (m, 4H), 6.97 (d, J=8.4 Hz, 2H), 3.89 (s, 3H).

Compound 3 (2.56 g, 10 mmol) was dissolved in N,N-dimethylformamide (20 ml), 1-bromo-2-chloroethane (1.03 ml, 12 mmol) and potassium carbonate (4.14 g, 30 mmol) were added, and reaction was performed at room temperature for 20 h. 200 mL of water was added to the reaction solution, and a large amount of brown-yellow solid precipitated. After suction filtration, the filter cake was washed 3 times with 10 ml of water, and an orange solid 4 was obtained after drying.

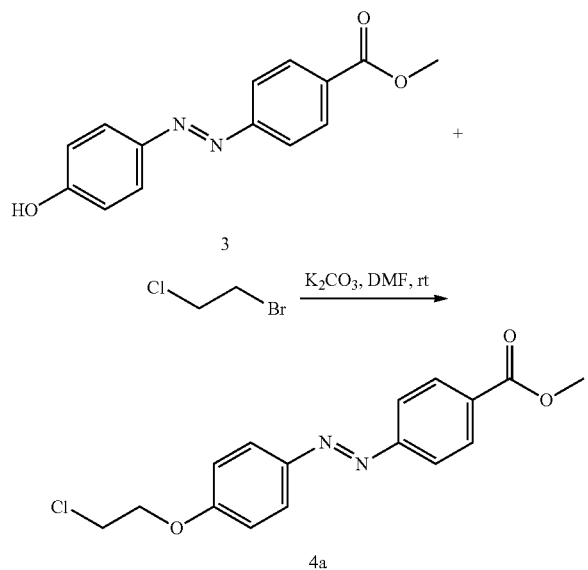

(E)-4-((4-(2-chloroethoxy)phenyl)diazenyl)methyl benzoate (4a)

1H NMR (300 MHz, DMSO-d6) δ 8.22-8.06 (m, 2H), 7.98-7.81 (m, 4H), 7.29-7.09 (m, 2H), 4.38 (t, J=11.2 Hz, 2H), 4.08-3.94 (m, 2H), 3.90 (s, 3H).

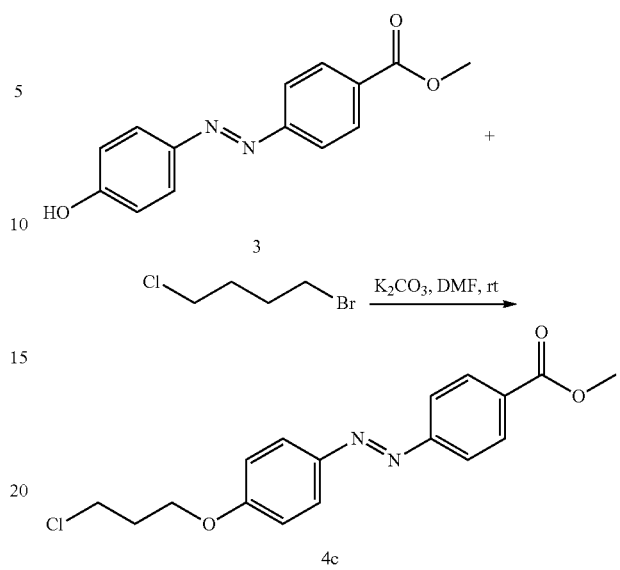

(E)-4-((4-(4-chlorobutoxy)phenyl)diazenyl)methyl benzoate (4c)

1H NMR (300 MHz, Chloroform-d) δ 8.17 (d, J=8.3 Hz, 2H), 7.92 (dd, J=11.4, 8.5 Hz, 4H), 7.01 (d, J=8.5 Hz, 2H), 4.09 (d, J=5.2 Hz, 2H), 3.95 (s, 3H), 3.63 (d, J=5.9 Hz, 2H), 2.01 (p, J=2.9 Hz, 4H).

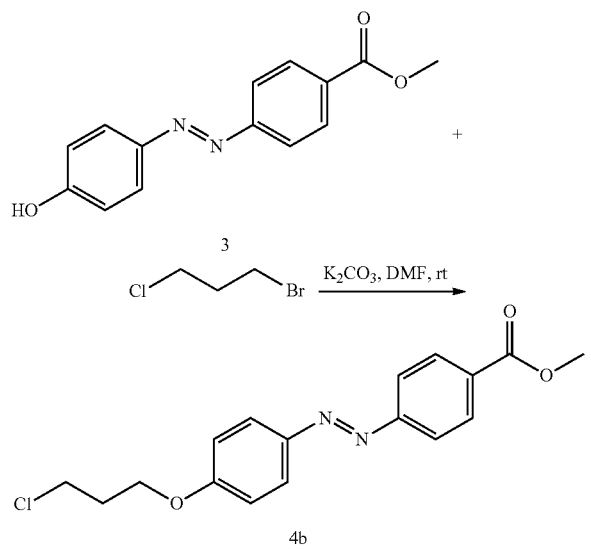

(E)-4-((4-(3-chloropropoxy)phenyl)diazenyl)methyl benzoate (4b)

1H NMR (300 MHz, Chloroform-d) δ 8.24-8.12 (m, 2H), 8.01-7.86 (m, 4H), 7.09-6.97 (m, 2H), 4.21 (t, J=5.8 Hz, 2H), 3.95 (s, 3H), 3.77 (t, J=6.2 Hz, 2H), 2.28 (p, J=6.0 Hz, 2H).

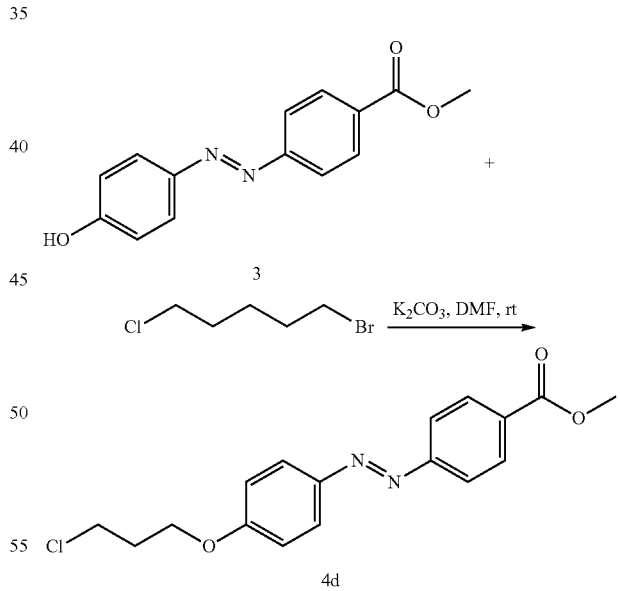

(E)-4-((4-((5-chloropentyl)oxy)phenyl)diazenyl) methyl benzoate (4d)

1H NMR (300 MHz, Chloroform-d) δ 8.17 (d, J=8.4 Hz, 2H), 7.99-7.85 (m, 4H), 7.06-6.96 (m, 2H), 4.07 (t, J=6.3 Hz, 2H), 3.95 (s, 3H), 3.59 (t, J=6.6 Hz, 2H), 1.95-1.80 (m, 4H), 1.66 (ddt, J=14.5, 9.7, 5.7 Hz, 2H).

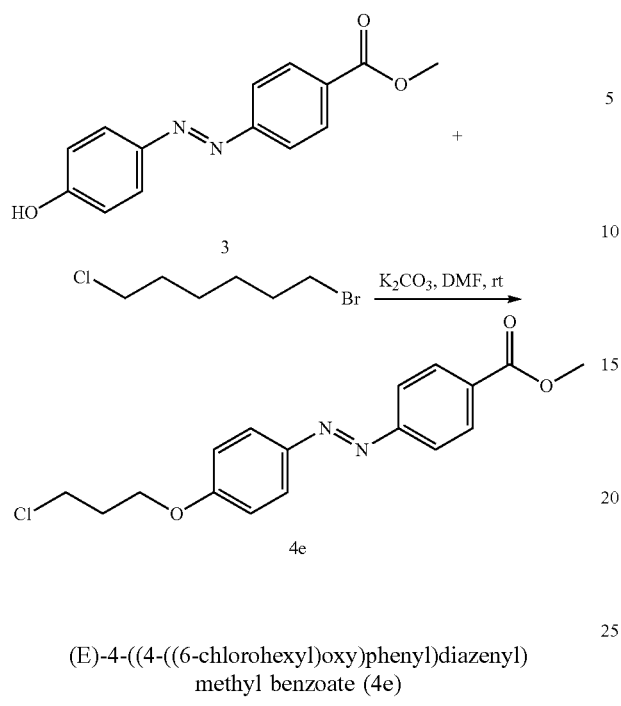

4e (E)-4-((4-((6-chlorohexyl)oxy)phenyl)diazenyl) methyl benzoate (4e)

1H NMR (300 MHz, DMSO-d6) δ 8.15 (d, J=8.0 Hz, 2H), 7.93 (d, J=8.2 Hz, 4H), 7.15 (d, J=8.4 Hz, 2H), 4.17-4.05 (m, 2H), 3.90 (s, 3H), 3.65 (s, 2H), 1.84-1.66 (m, 4H), 1.56-1.38 (m, 4H).

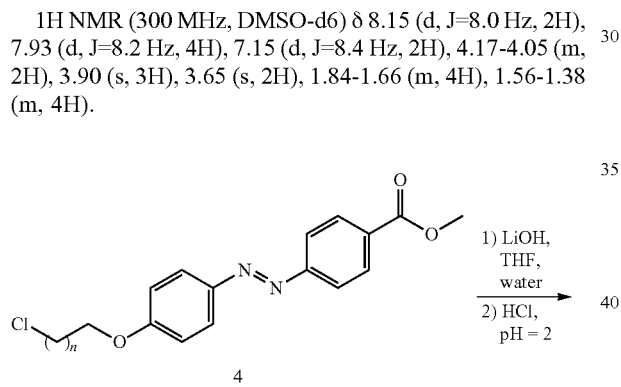

Compound 4 (5 mmol) was dissolved in 10 ml of tetrahydrofuran, 10 ml of aqueous solution of lithium hydroxide (600 mg, 25 mmol) was slowly added, and the reaction solution was stirred overnight at room temperature. After the reaction was completed, 200 mL of water was added to the reaction solution under stirring, the system was adjusted to pH=2 with dilute hydrochloric acid, and a large amount of orange solid precipitated. A crude product was obtained by suction filtration, the filter cake was washed with water 3 times, and an orange solid 5 was obtained after drying.

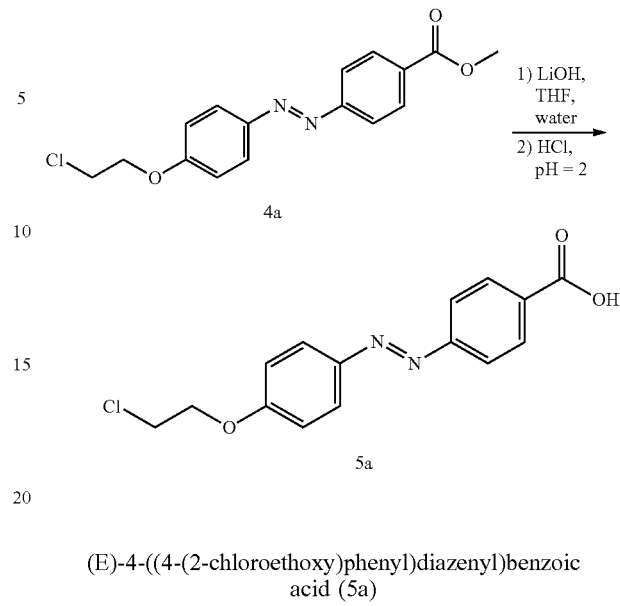

(E)-4-((4-(2-chloroethoxy)phenyl)diazenyl)benzoic acid (5a)

1H NMR (300 MHz, DMSO-d6) δ 13.40-12.80 (s, 1H), 8.32-8.10 (m, 2H), 8.06-7.81 (m, 4H), 7.29-7.09 (m, 2H), 4.38 (t, J=10.8 Hz, 2H), 4.12-3.92 (m, 2H).

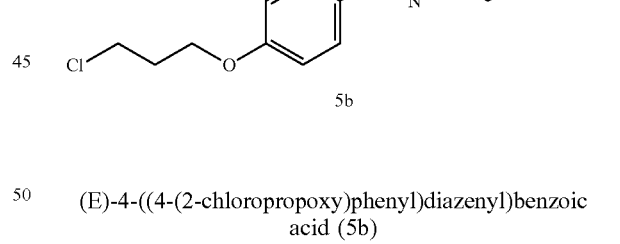

(E)-4-((4-(2-chloropropoxy)phenyl)diazenyl)benzoic acid (5b)

1H NMR (300 MHz, DMSO-d6) δ 8.06 (d, J=8.1 Hz, 2H), 7.90 (d, J=8.5 Hz, 2H), 7.78 (d, J=8.1 Hz, 2H), 7.16 (d, J=8.5 Hz, 2H), 5.76 (s, 2H), 4.21 (t, J=6.1 Hz, 2H), 3.82 (t, J=6.5 Hz, 2H), 2.22 (p, J=6.4 Hz, 2H).

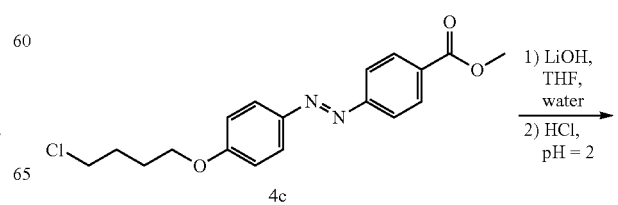

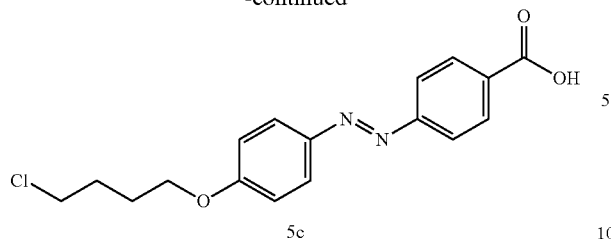
(E)-4-((4-(2-chlorobutoxy)phenyl)diazenyl)benzoic acid (5c)
1H NMR (300 MHz, DMSO-d6) δ 8.04 (d, J=8.0 Hz, 2H), 7.90 (d, J=8.6 Hz, 2H), 7.78 (d, J=8.1 Hz, 2H), 7.14 (d, J=8.5 Hz, 2H), 4.13 (d, J=5.2 Hz, 2H), 1.97-1.77 (m, 4H).
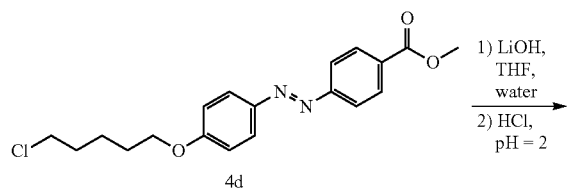
(E)-4-((4-(2-chloropentyloxy)phenyl)diazenyl)benzoic acid (5d)
1H NMR (300 MHz, DMSO-d6) δ 8.09 (d, J=8.0 Hz, 2H), 7.86 (dd, J=25.2, 8.2 Hz, 4H), 7.13 (d, J=8.5 Hz, 2H), 4.10 (t, J=6.4 Hz, 2H), 3.68 (d, J=13.2 Hz, 2H), 1.79 (dq, J=12.5, 5.6 Hz, 4H), 1.57 (q, J=7.9 Hz, 2H).
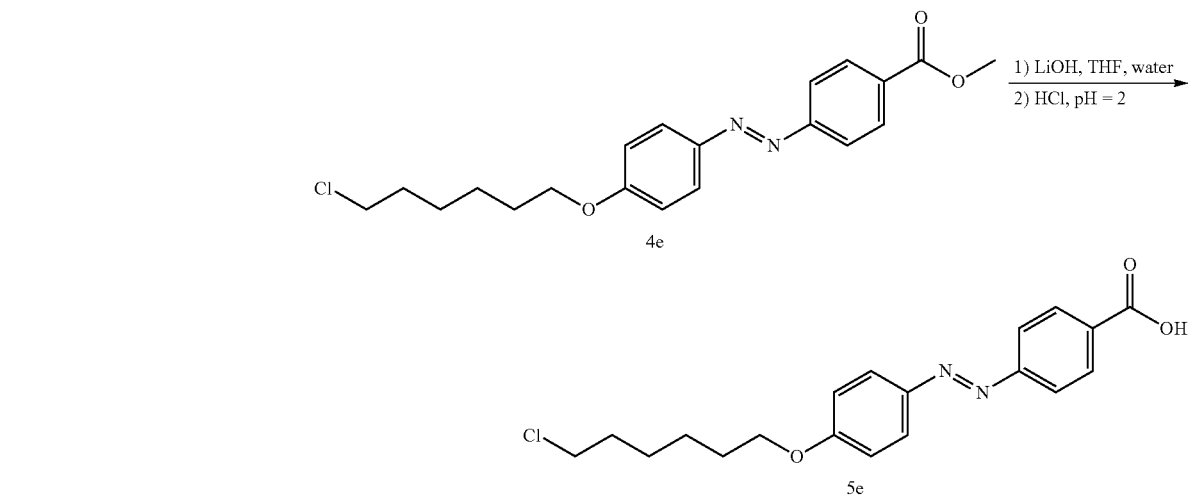
(E)-4-((4-(2-chlorohexyloxy)phenyl)diazenyl)benzoic acid (5e)
1H NMR (300 MHz, DMSO-d6) δ 8.04 (d, J=7.9 Hz, 2H), 7.88 (d, J=8.4 Hz, 2H), 7.77 (d, J=7.9 Hz, 2H), 7.12 (d, J=8.5 Hz, 2H), 4.07 (d, J=6.6 Hz, 2H), 3.64 (t, J=6.7 Hz, 2H), 1.75 (s, 4H), 1.46 (s, 4H).
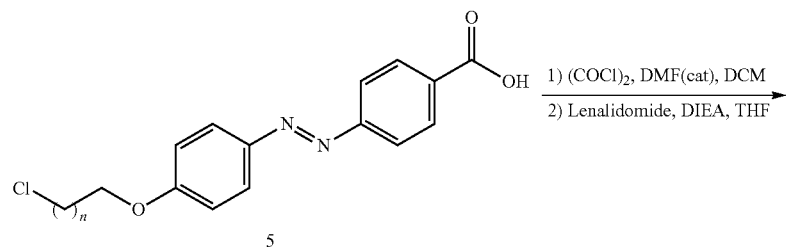

-continued

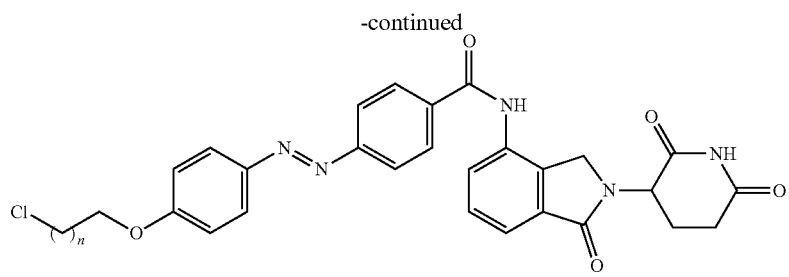

6

Compound 5 (2.0 mmol) was dissolved in anhydrous tetrahydrofuran (10 ml), oxalyl chloride (338 μl, 4.0 mmol) was added, 1 drop of N,N-dimethylformamide was added, and the reaction solution was stirred at room temperature for 30 minutes. After distillation under reduced pressure, the system was dissolved in anhydrous tetrahydrofuran (5 ml), a solution of lenalidomide (518.5 mg, 2.0 mmol) and DIEA (992 μl, 6.0 mmol) in tetrahydrofuran (20 ml) was added dropwise under ice bath, and the reaction solution was stirred overnight at room temperature. After the reaction was completed, a brown solid was obtained by distillation under reduced pressure, and the crude product was recrystallized with methanol to obtain compound 6, an orange solid.

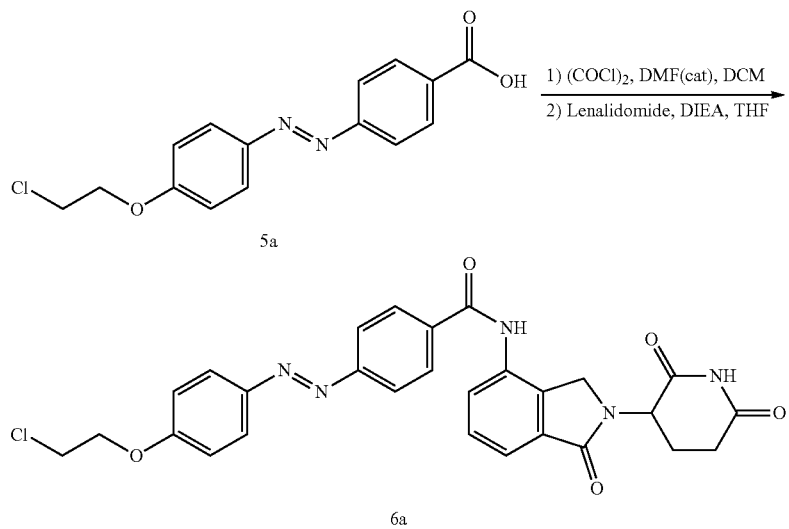

(E)-4-((4-(2-chloroethoxy)phenyl)diazenyl)-N-(2-(2,6-dioxopiperidin-3-yl)-1-oxoisoindole-4-yl)benzamide (6a)

1H NMR (300 MHz, DMSO-d6) δ 10.96 (s, 1H), 10.48 (s, 1H), 8.18 (d, J=8.2 Hz, 2H), 7.96 (dt, J=8.9, 4.2 Hz, 4H), 7.76 (d, J=7.5 Hz, 1H), 7.65-7.55 (m, 2H), 7.26-7.14 (m, 2H), 5.15 (dd, J=13.2, 5.2 Hz, 1H), 4.47 (d, J=2.6 Hz, 2H), 4.40 (t, J=5.1 Hz, 2H), 4.00 (t, J=5.1 Hz, 2H), 2.99-2.81 (m, 1H), 2.67-2.54 (m, 1H), 2.45-2.27 (m, 1H), 2.07-1.93 (m, 1H).

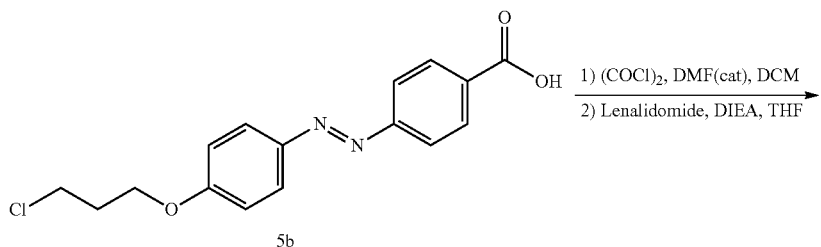
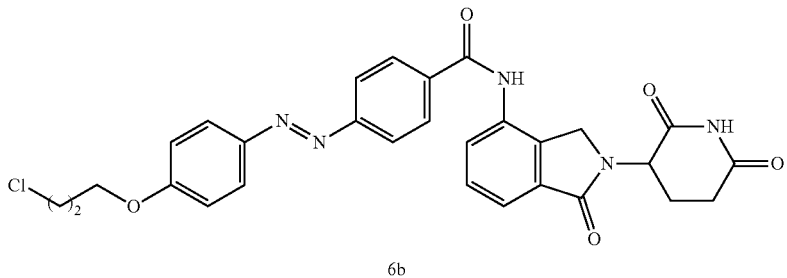
(E)-4-((4-(2-chloropropoxy)phenyl)diazenyl)-N-(2-(2,6-dioxopiperidin-3-yl)-1-oxoisoindole-4-yl)benzamide (6b)
1H NMR (300 MHz, DMSO-d6) δ 10.99 (s, 1H), 10.51 (s, 1H), 8.19 (d, J=8.2 Hz, 2H), 7.97 (dd, J=8.4, 5.8 Hz, 4H), 7.77 (d, J=7.5 Hz, 1H), 7.60 (dt, J=15.2, 7.5 Hz, 2H), 7.19 (d, J=8.6 Hz, 2H), 5.17 (dd, J=13.2, 5.0 Hz, 1H), 4.54-4.38 (m, 2H), 4.23 (t, J=6.0 Hz, 2H), 3.83 (t, J=6.5 Hz, 2H), 2.99-2.82 (m, 1H), 2.64-2.54 (m, 1H), 2.45-2.34 (m, 1H), 2.23 (p, J=6.5 Hz, 2H), 2.04-1.97 (m, 1H).
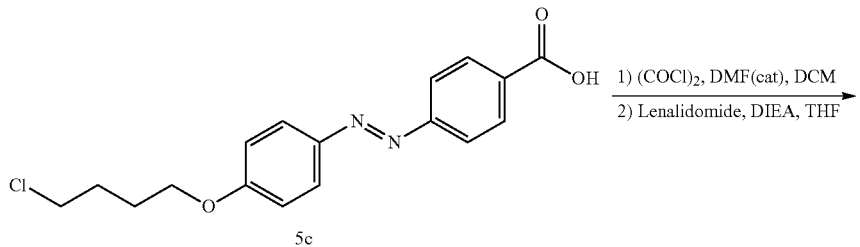
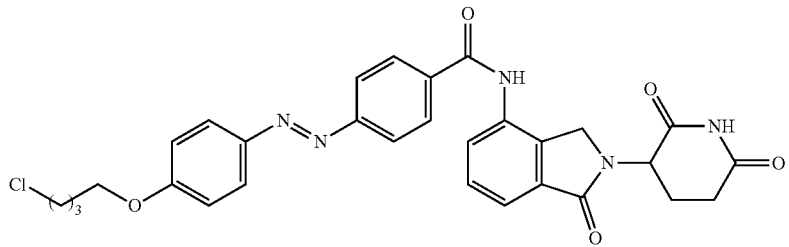
(E)-4-((4-(2-chlorobutoxy)phenyl)diazenyl)-N-(2-(2,6-dioxopiperidin-3-yl)-1-oxoisoindole-4-yl)benzamide (6c)
1H NMR (300 MHz, DMSO-d6) δ 11.01 (s, 1H), 10.53 (s, 1H), 8.15 (dd, J=18.7, 8.2 Hz, 2H), 7.94 (dd, J=11.3, 8.3 Hz, 4H), 7.77 (d, J=7.4 Hz, 1H), 7.60 (dt, J=14.9, 7.4 Hz, 2H), 7.16 (dd, J=9.2, 2.8 Hz, 2H), 5.17 (dd, J=13.5, 4.9 Hz, 1H), 4.47 (s, 2H), 4.15 (s, 2H), 3.73 (d, J=6.5 Hz, 2H), 2.99-2.85 (m, 1H), 2.66-2.55 (m, 1H), 2.48-2.33 (m, 1H), 2.07-1.98 (m, 1H), 1.96-1.79 (m, 4H).

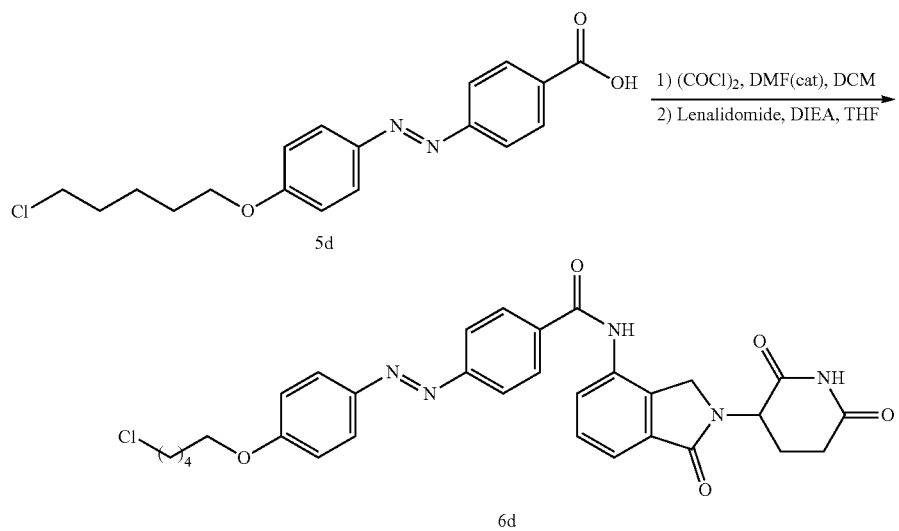

(E)-4-((4-(2-chloropentyloxy)phenyl)diazenyl)-N-(2-(2,6-dioxopiperidin-3-yl)-1-oxoisoindole-4-yl)benzamide (6d)

1H NMR (300 MHz, DMSO-d6) δ 10.90 (s, 1H), 10.42 (s, 1H), 8.09 (d, J=8.2 Hz, 2H), 7.87 (t, J=7.9 Hz, 4H), 7.67 (d, J=7.5 Hz, 1H), 7.51 (dt, J=15.1, 7.5 Hz, 2H), 7.07 (d, J=8.5 Hz, 2H), 5.07 (dd, J=13.1, 5.2 Hz, 1H), 4.43-4.33 (m, 2H), 4.03 (t, J=6.3 Hz, 2H), 3.59 (t, J=6.5 Hz, 2H), 2.90-2.80 (m, 1H), 2.62-2.48 (m, 1H), 2.46-2.32 (m, 1H), 1.99-1.87 (m, 1H), 1.70 (d, J=9.7 Hz, 4H), 1.47 (t, J=7.8 Hz, 2H).

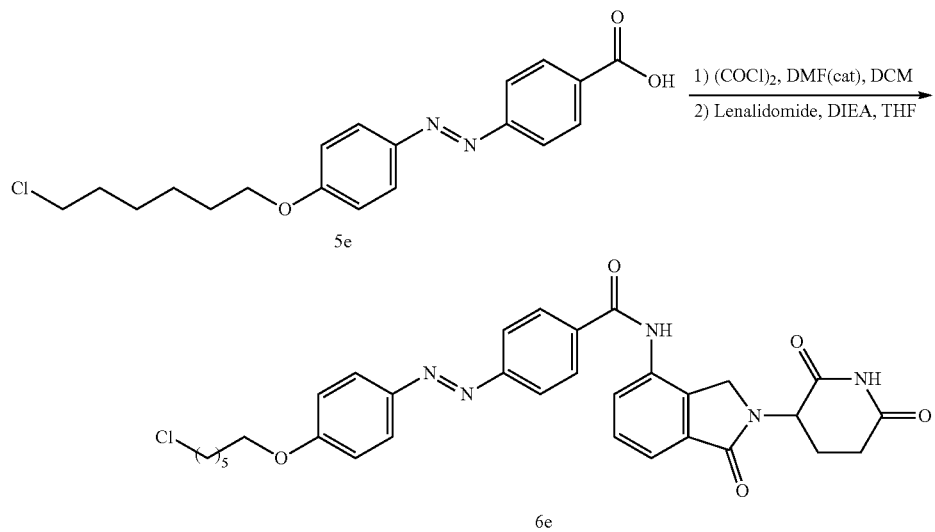

(E)-4-((4-(2-chlorohexyloxy)phenyl)diazenyl)-N-(2-(2,6-dioxopiperidin-3-yl)-1-oxoisoindole-4-yl)benzamide (6e)

1H NMR (300 MHz, DMSO-d6) δ 11.00 (s, 1H), 10.52 (s, 1H), 8.18 (d, J=8.3 Hz, 2H), 7.95 (t, J=8.2 Hz, 4H), 7.76 (d, J=7.4 Hz, 1H), 7.60 (dt, J=15.0, 7.4 Hz, 2H), 7.15 (d, J=8.6 Hz, 2H), 5.16 (dd, J=13.1, 5.1 Hz, 1H), 4.54-4.40 (m, 2H), 4.10 (t, J=6.5 Hz, 2H), 3.65 (t, J=6.6 Hz, 2H), 2.96-2.84 (m, 1H), 2.68-2.52 (m, 1H), 2.46-2.33 (m, 1H), 2.04-1.98 (m, 1H), 1.88-1.62 (m, 4H), 1.47 (d, J=7.1 Hz, 4H).

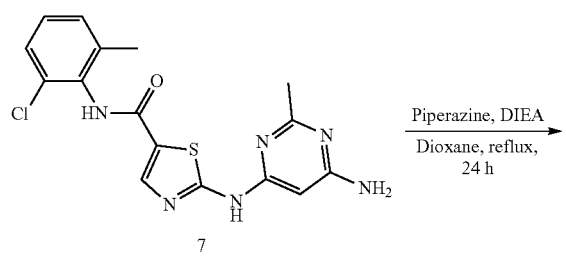
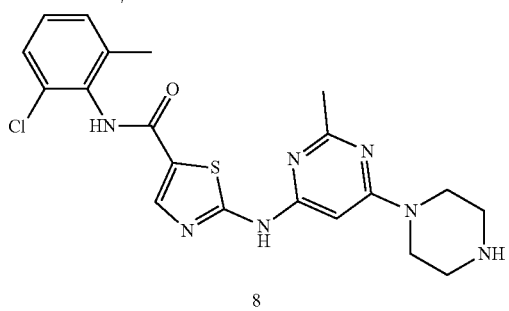

N-(2-chloro-6-methylphenyl)-2-(2-methyl-6-(piperazin-1-yl)pyrimidin-4-ylamino)thiazole-5-carboxamide (8)

2-(6-chloro-2-methylpyrimidin-4-ylamino)-N-(2-chloro-6-methylphenyl)thiazole-5-carboxamide, 7 (1.00 g, 2.54 mmol), piperazin (2.19 g, 25.4 mmol), and N,N-diisopropylethylamine (0.84 mL, 5.07 mmol) were dissolved in anhydrous 1,4-dioxane (30 ml), and the reaction solution was refluxed for 12 hours. An oily substance obtained by distillation under reduced pressure was washed with water/methanol and methanol/ether sequentially to obtain an off-white solid. The crude product was recrystallized with ether to obtain compound 8 (0.82 g, 73%).

1H NMR (300 MHz, DMSO-d6) δ 9.88 (s, 1H), 8.21 (s, 1H), 7.40 (d, J=7.3 Hz, 1H), 7.26 (d, J=8.2 Hz, 2H), 6.02 (s, 1H), 3.44 (s, 4H), 2.74 (s, 4H), 2.40 (d, J=3.0 Hz, 3H), 2.23 (d, J=2.9 Hz, 3H).

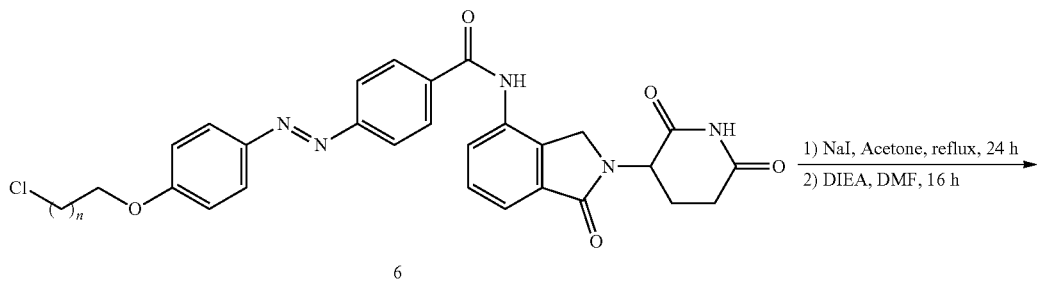

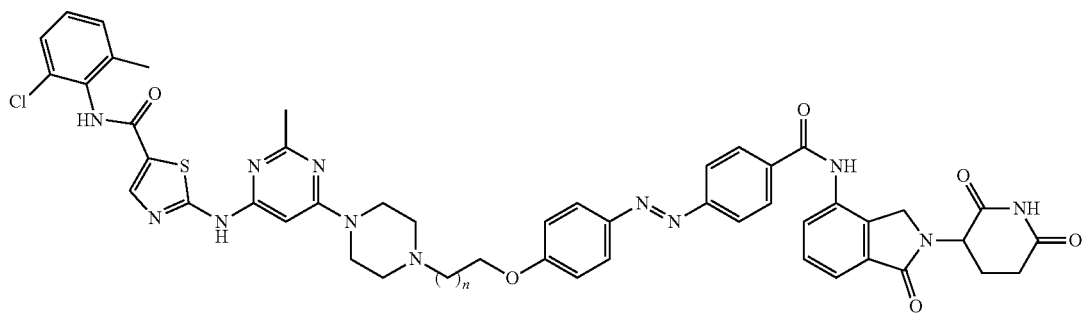

Sodium iodide (83 mg, 0.55 mmol) was added to a solution of intermediate 6 (0.11 mmol) in acetone (10 ml), and the reaction solution was refluxed for 24 hours and distilled under reduced pressure to obtain an orange solid. The solid was dissolved in DMF (20 ml), compound 8 (43 mg, 0.10 mmol) and DIEA (96 μL, 0.57 mmol) were sequentially added, and the reaction solution was stirred at 80° C. for 16 hours. The reaction solution was cooled to room temperature, 200 mL of water was added, and an orange solid precipitated. After suction filtration, the crude product was purified by TLC (MeOH/DCM, 1/50 to 1/25) to obtain compound 9, an orange solid.

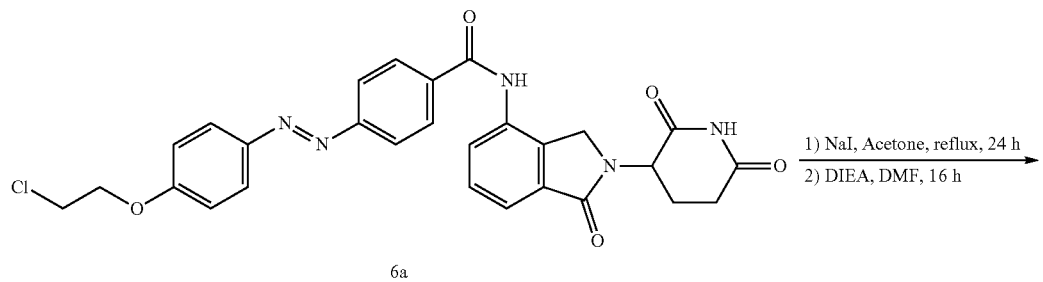
6a
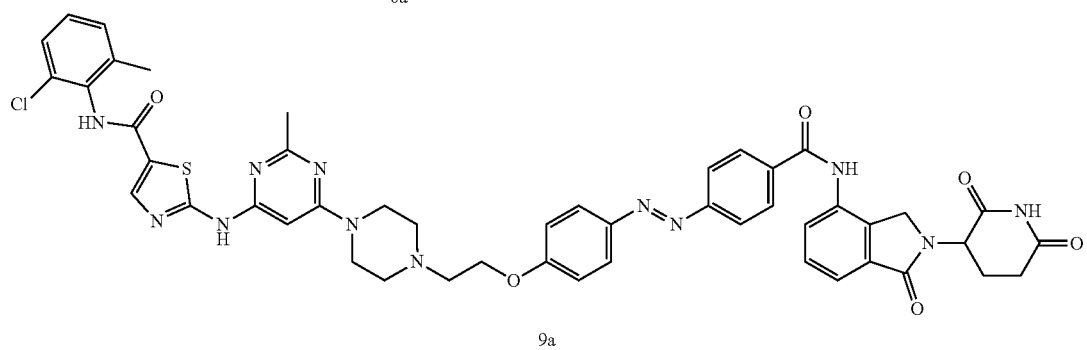
9a
(E)-N-(2-chloro-6-methylphenyl)-2-((6-(4-(2-(4-((4-((2-(2,6-dioxopiperidin-3-yl)-1-oxoisoindolin-4-yl)carbamoyl)phenyl)diazenyl)phenoxy)ethyl)piperazin-1-yl)-2-methylpyrimidin-4-yl)amino)thiazole-5-carboxamide (9a)
$^1$H NMR (300 MHz, DMSO-d$_6$) δ 11.47 (s, 1H), 10.99 (s, 1H), 10.51 (s, 1H), 9.87 (s, 1H), 8.26-8.13 (m, 3H), 8.06-7.85 (m, 4H), 7.75 (d, J=7.4 Hz, 1H), 7.68-7.46 (m, 2H), 7.38 (d, J=7.4 Hz, 1H), 7.32-7.15 (m, 4H), 6.05 (s, 1H), 5.15 (dd, J=13.2, 5.2 Hz, 1H), 4.43 (d, J=16.4 Hz, 2H), 4.25 (d, J=5.1 Hz, 2H), 3.59-3.46 (m, 4H), 2.99-2.88 (m, 1H), 2.77-2.67 (m, 1H), 2.63-2.53 (m, 4H), 2.40 (s, 3H), 2.36-2.30 (m, 1H), 2.22 (s, 3H), 2.06-1.91 (m, 1H). MS(ESI): calcd for C$_{48}$H$_{45}$ClN$_{12}$O$_6$S, 952.30; m/z: [M]$^+$=953.3036
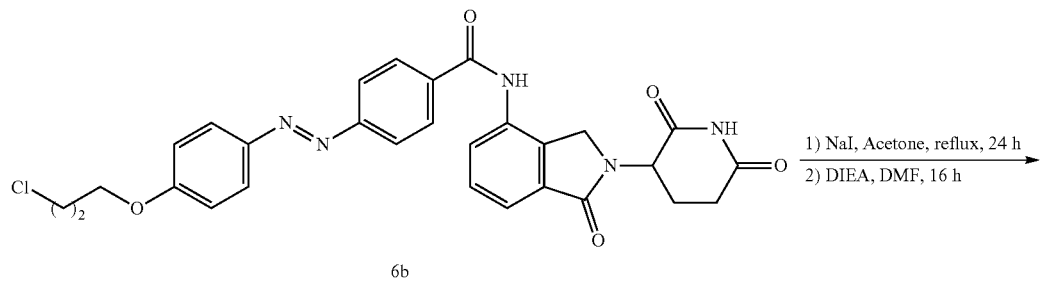
6b
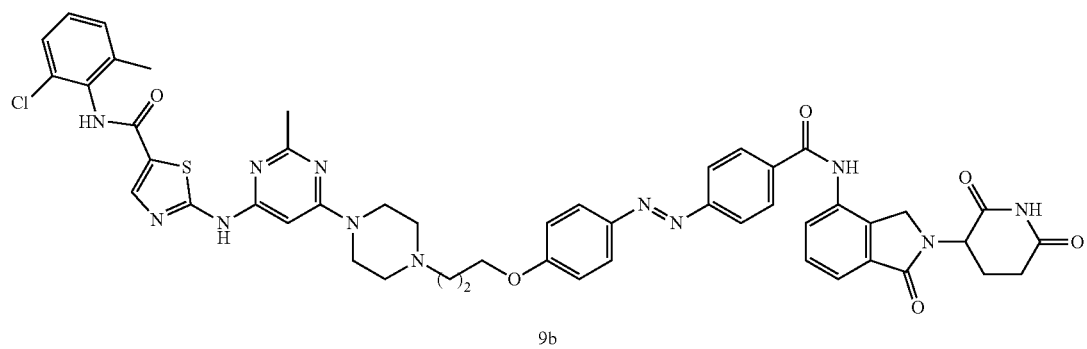
9b (E)-N-(2-chloro-6-methylphenyl)-2-((6-(4-(3-(4-((4-((2-(2,6-dioxopiperidin-3-yl)-1-oxoisoindolin-4-yl)carbamoyl)phenyl)diazenyl)phenoxy)propyl)piperazin-1-yl)-2-methylpyrimidin-4-yl)amino)thiazole-5-carboxamide (9b)

¹H NMR (300 MHz, DMSO-d₆) 11.47 (s, 1H), 10.99 (s, 1H), 10.51 (s, 1H), 9.87 (s, 1H), 8.25-8.11 (m, 3H), 7.95 (dd, J=8.5, 5.9 Hz, 4H), 7.75 (d, J=7.4 Hz, 1H), 7.60 (dd, J=13.7, 7.4 Hz, 2H), 7.38 (dd, J=7.3, 2.1 Hz, 1H), 7.31-7.12 (m, 4H), 6.04 (s, 1H), 5.15 (dd, J=13.2, 5.2 Hz, 1H), 4.46 (s, 2H), 4.23-4.12 (m, 2H), 3.59-3.46 (m, 4H), 2.96-2.85 (m, 1H), 2.63-2.60 (m, 1H), 2.57-2.49 (m, 4H), 2.39 (s, 3H), 2.32-2.25 (m, 1H), 2.22 (s, 3H), 2.07-1.88 (m, 3H). MS(ESI): calcd for $C_{49}H_{47}ClN_{12}O_6S$, 966.32; m/z [M]+: 967.3325

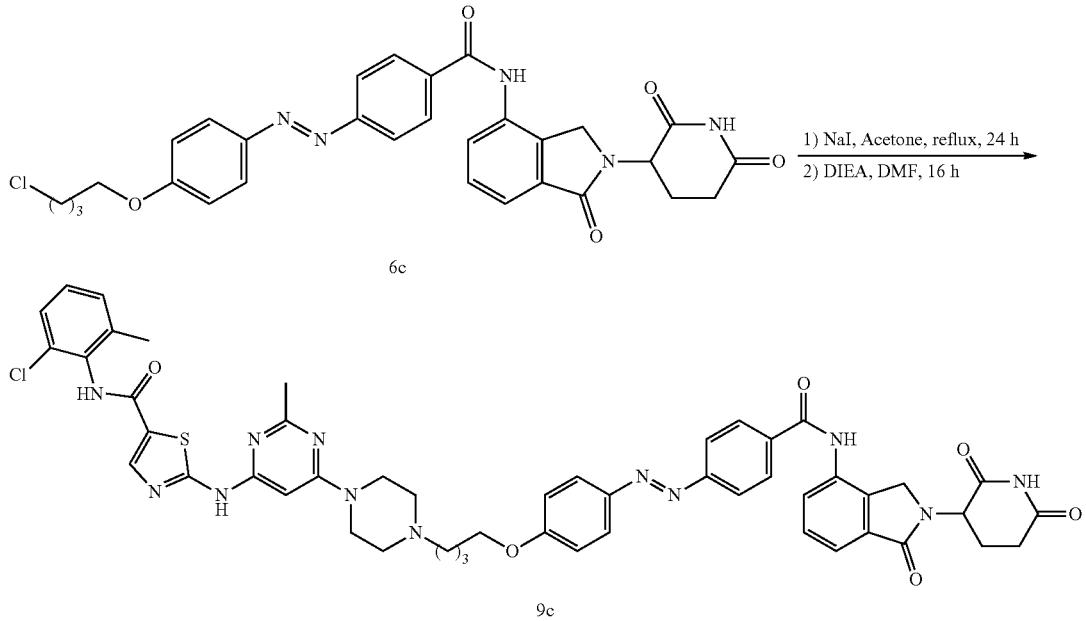

(E)-N-(2-chloro-6-methylphenyl)-2-((6-(4-(4-(4-((4-((2-(2,6-dioxopiperidin-3-yl)-1-oxoisoindolin-4-yl)carbamoyl)phenyl)diazenyl)phenoxy)butyl)piperazin-1-yl)-2-methylpyrimidin-4-yl)amino)thiazole-5-carboxamide (9c)

¹H NMR (300 MHz, DMSO-d₆) δ 11.41 (s, 1H), 10.96 (s, 1H), 10.44 (d, J=15.3 Hz, 1H), 9.83 (s, 1H), 8.30-8.09 (m, 3H), 7.95 (t, J=7.4 Hz, 4H), 7.80 (dd, J=18.2, 7.5 Hz, 1H), 7.58 (h, J=8.5, 7.9 Hz, 3H), 7.38 (d, J=7.4 Hz, 1H), 7.25 (d, J=8.2 Hz, 2H), 7.16 (d, J=8.8 Hz, 2H), 6.05 (d, J=6.7 Hz, 1H), 5.15 (dd, J=13.6, 5.2 Hz, 1H), 4.50 (d, J=17.5 Hz, 2H), 4.13 (d, J=6.6 Hz, 2H), 3.55-3.49 (m, 4H), 3.05-2.79 (m, 1H), 2.66-2.54 (m, 1H), 2.44 (s, 3H), 2.43-2.33 (m, 4H), 2.32-2.26 (m, 1H), 2.25-2.19 (s, 3H), 2.10-1.95 (m, 1H), 1.89-1.71 (m, 2H), 1.63 (t, J=7.9 Hz, 2H). MS(ESI): calcd for $C_{50}H_{49}ClN_{12}O_6S$, 980.33; m/z: [M]⁺=981.33728

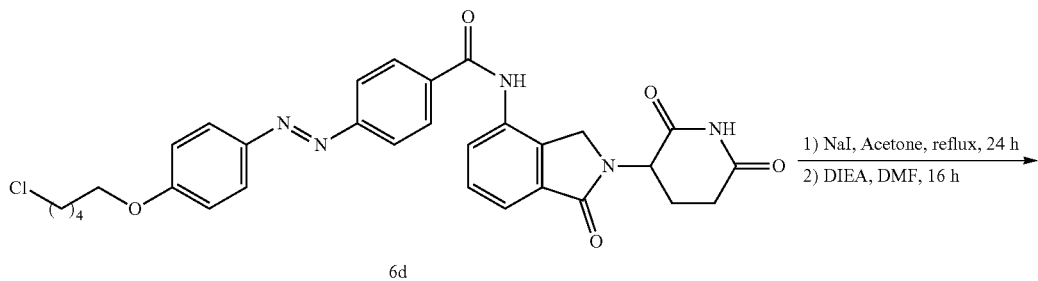

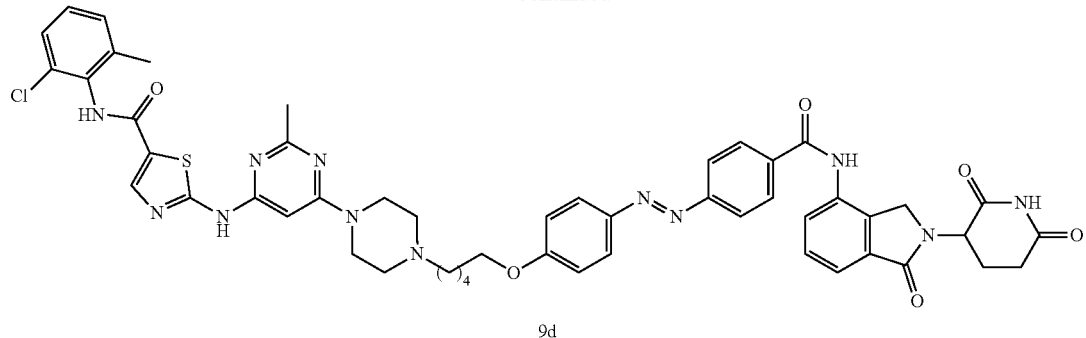

9d (E)-N-(2-chloro-6-methylphenyl)-2-((6-(4-(5-(4-((2-(2,6-dioxopiperidin-3-yl)-1-oxoisoindolin-4-yl)carbamoyl)phenyl)diazenyl)phenoxy)pentyl)piperazin-1-yl)-2-methylpyrimidin-4-yl)amino)thiazole-5-carboxamide (9d)

$^1$H NMR (300 MHz, DMSO-d$_6$) δ 11.46 (s, 1H), 10.99 (s, 1H), 10.51 (s, 1H), 9.86 (s, 1H), 8.25-8.12 (m, 3H), 7.95 (t, J=7.7 Hz, 4H), 7.75 (d, J=7.4 Hz, 1H), 7.60 (dd, J=13.6, 7.2 Hz, 2H), 7.38 (d, J=7.4 Hz, 1H), 7.25 (d, J=7.9 Hz, 2H), 7.15 (d, J=8.6 Hz, 2H), 6.03 (s, 1H), 5.15 (dd, J=12.2, 5.2 Hz, 1H), 4.50-4.37 (m, 2H), 4.09 (d, J=6.7 Hz, 2H), 3.60-3.41 (m, 4H), 2.98-2.82 (m, 1H), 2.64-2.53 (m, 1H), 2.42 (s, 3H), 2.41-2.34 (m, 4H), 2.33-2.27 (m, 1H), 2.22 (s, 3H), 2.01-1.94 (m, 1H), 1.85-1.70 (m, 2H), 1.57-1.43 (s, 4H). MS(ESI): calcd for C$_{51}$H$_{51}$ClN$_{12}$O$_6$S 994.35; m/z: [M]$^+$=995.3535

(E)-N-(2-chloro-6-methylphenyl)-2-((6-(4-(6-(4-((2-(2,6-dioxopiperidin-3-yl)-1-oxoisoindolin-4-yl)carbamoyl)phenyl)diazenyl)phenoxy)hexyl)piperazin-1-yl)-2-methylpyrimidin-4-yl)amino)thiazole-5-carboxamide (9e)

$^1$H NMR (300 MHz, DMSO-d$_6$) δ 11.39 (s, 1H), 10.92 (s, 1H), 10.41 (s, 1H), 9.80 (s, 1H), 8.25-8.02 (m, 3H), 7.90 (t, J=8.1 Hz, 4H), 7.73 (p, J=10.2, 8.7 Hz, 1H), 7.54 (dt, J=15.6, 7.8 Hz, 2H), 7.34 (d, J=7.3 Hz, 1H), 7.20 (d, J=8.3 Hz, 2H), 7.09 (d, J=8.6 Hz, 2H), 6.00 (s, 1H), 5.11 (dd, J=13.1, 5.2 Hz, 1H), 4.50-4.34 (m, 2H), 4.04 (t, J=6.4 Hz, 2H), 3.46 (d, J=6.7 Hz, 4H), 2.96-2.78 (m, 1H), 2.61-2.53 (m, 1H), 2.41-2.31 (m, 4H), 2.26 (s, 3H), 2.21-2.11 (m, 4H), 2.01-1.87 (m, 1H), 1.79-1.64 (m, 2H), 1.42 (q, J=7.1 Hz, 4H), 1.34 (d, J=9.6 Hz, 2H). MS (ESI): calcd for C$_{52}$H$_{53}$ClN$_{12}$O$_6$S 1008.36; m/z: [M]$^+$=1009.36956

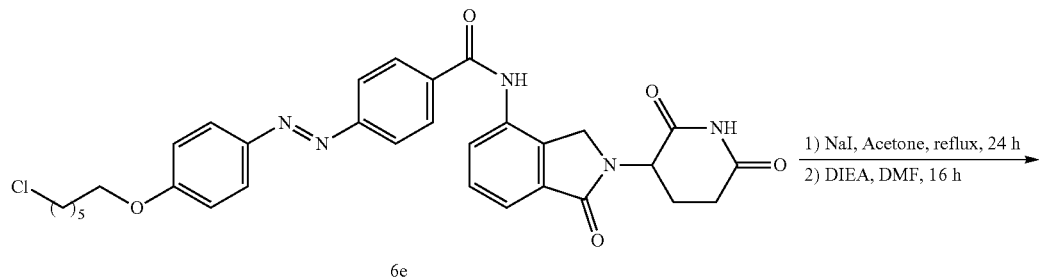

6e

1) NaI, Acetone, reflux, 24 h
2) DIEA, DMF, 16 h

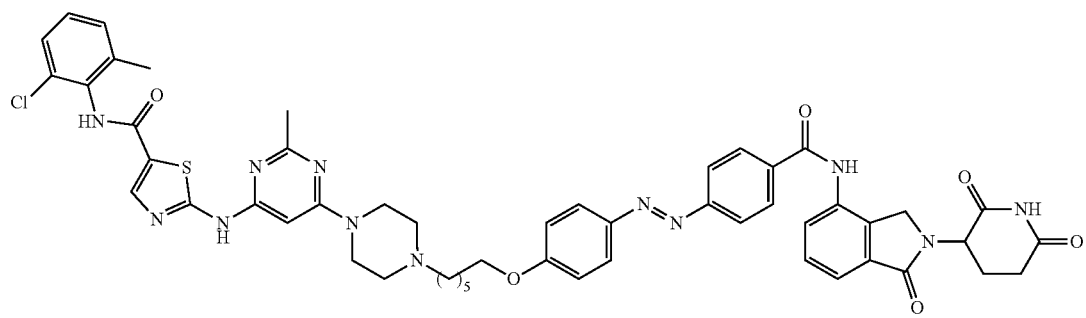

9e

Example 2: Effect Example

Figure 2A:
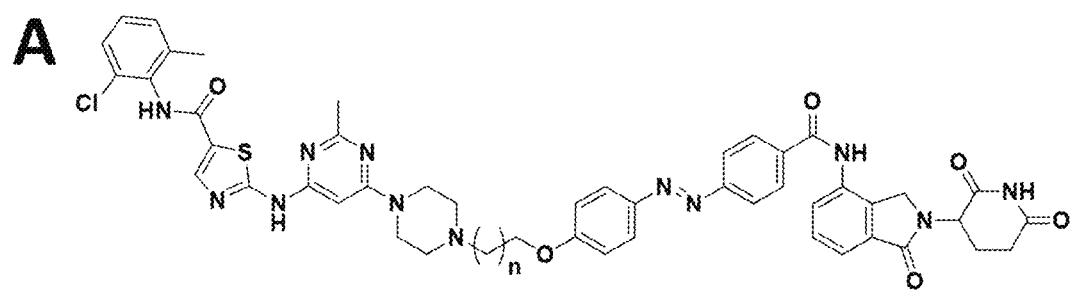
FIG. 2A shows the chemical structures of compounds 2C-6C.
Figure 2B:
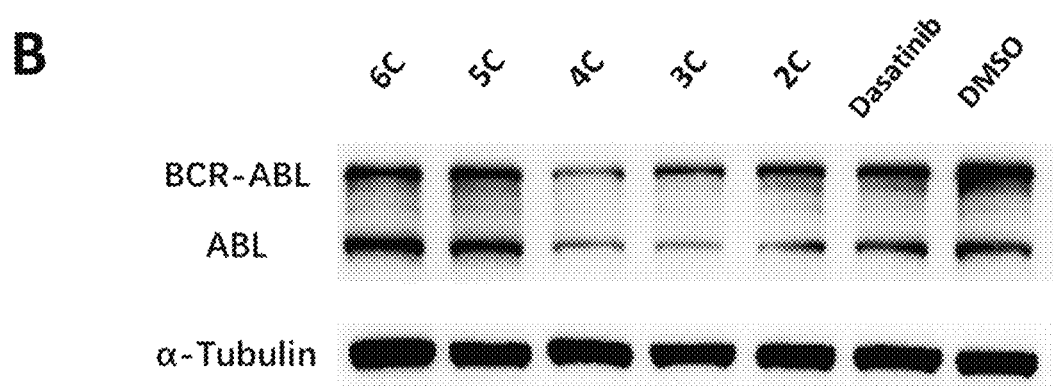
FIG. 2B shows immunoblotting detection images for the activity in degradation of ABL and BCR-ABL proteins in BCR-ABL and CRBN positive K562 cell lines (treated with compound 4C)
Figure 2C:
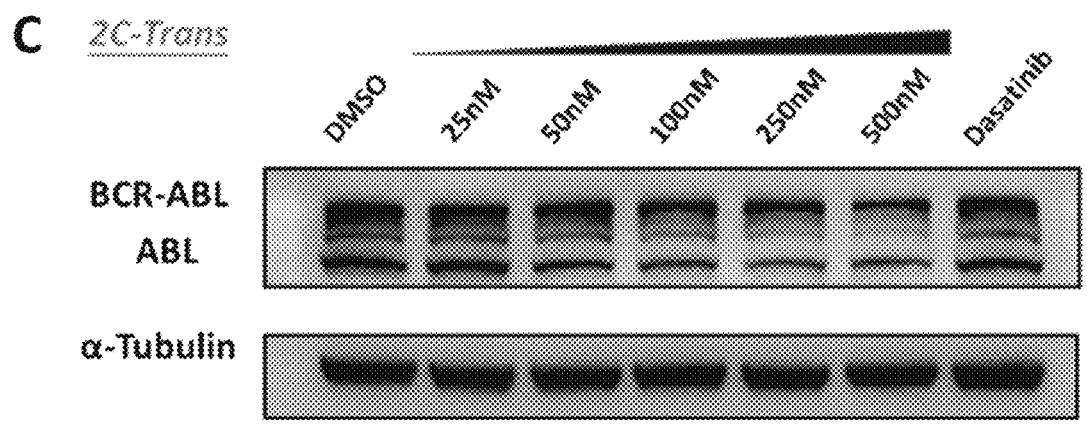
FIG. 2C shows immunoblotting detection images for the activity in degradation of ABL and BCR-ABL proteins in BCR-ABL and CRBN positive K562 cell lines (treated with compound 2C)
Figure 2D:
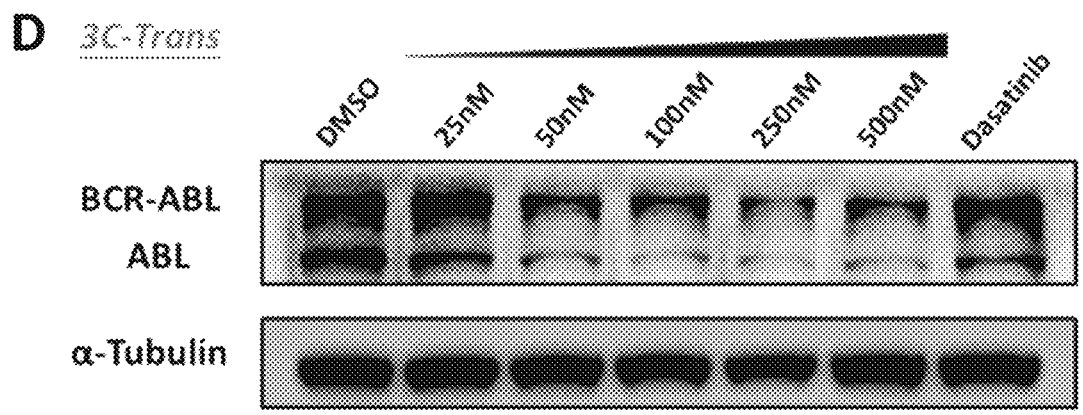
FIG. 2D shows immunoblotting detection images for the activity in degradation of ABL and BCR-ABL proteins in BCR-ABL and CRBN positive K562 cell lines (treated with compound 3C)
Figure 2E:
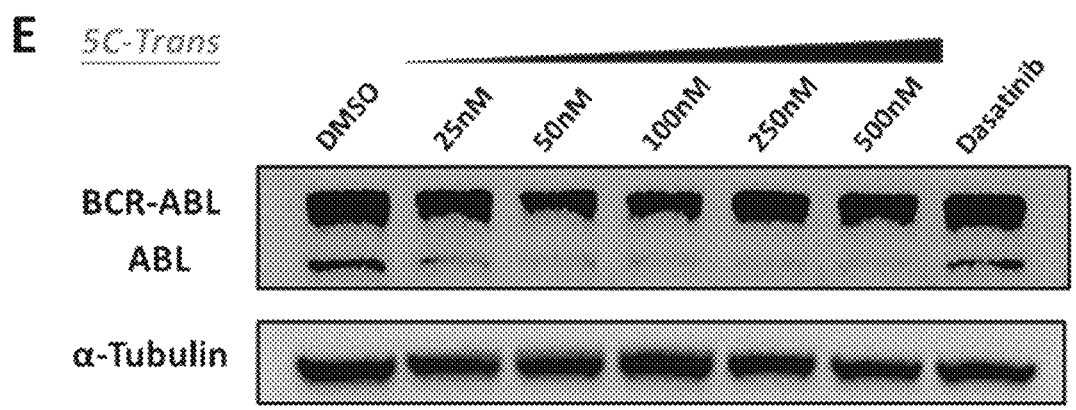
FIG. 2E shows immunoblotting detection images for the activity in degradation of ABL and BCR-ABL proteins in BCR-ABL and CRBN positive K562 cell lines (treated with compound 5C)
Figure 2F:
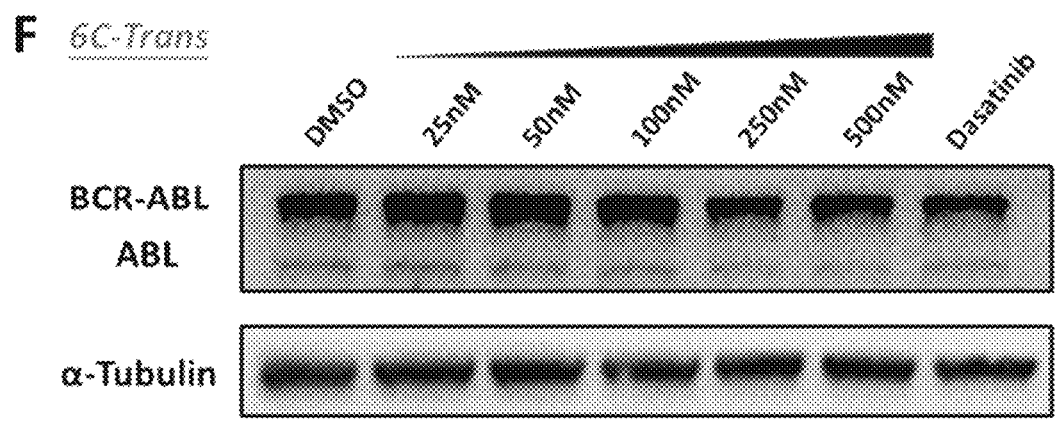
FIG. 2F shows immunoblotting detection images for the activity in degradation of ABL and BCR-ABL proteins in BCR-ABL and CRBN positive K562 cell lines (treated with compound 6C)
Figure 5A:
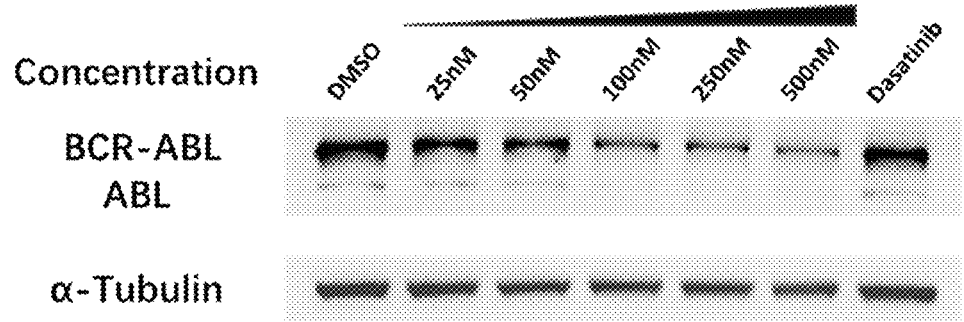
FIG. 5A shows immunoblotting-dose effect experiment of compound 4C-trans after 24 hours of incubation.

Initially, researchers synthesized a 2C compound (FIG. 2A), which is a small molecule with the shortest joining chain (n=1). By using BCR-ABL and CRBN positive K562 cell lines, degradation of ABL and BCR-ABL proteins in the cells under the action of the compound was tested by immunoblotting. 36 hours after administration, WB results showed that the compound 2C can down-regulate the level of the BCR-ABL protein in a dose-dependent manner, and the levels of the ABL protein and BCR-ABL fusion protein at a concentration of 100 nM were significantly reduced (FIG. 2C). Then, the researchers tried to extend the joining chain (increasing the value of n). The results showed that as the linker extended to 4 carbon atoms, the degradation activity of the compound continued to increase, but the activity gradually decreased when the chain length was further extended. Among these PROTAC molecules, a compound 4C showed the best activity in degrading the BCR-ABL fusion protein (FIG. 2B). FIG. 2D shows the dose-effect relationship between a 3C compound and the degradation of the ABL and BCR-ABL proteins in the K562 cell line. FIG. 5A shows the dose-effect relationship between the 4C compound and the degradation of the ABL and BCR-ABL proteins in the K562 cell line. FIG. 2E shows the dose-effect relationship between a 5C compound and the degradation of the ABL and BCR-ABL proteins in the K562 cell line. FIG. 2F shows the dose-effect relationship between a 6C compound and the degradation of ABL and BCR-ABL proteins in the K562 cell line.

The above test shows that all the proteolysis targeting chimeric molecules 2C, 3C, 4C, 5C and 6C can inhibit the expression of BCR-ABL and/or CRBN protein in BCR-ABL and/or CRBN positive leukemia K562 cells to varying degrees, and thus can be used to prepare drugs for treating BCR-ABL and/or CRBN positive leukemia.

Example 3: Effect Example

Figure 3A:
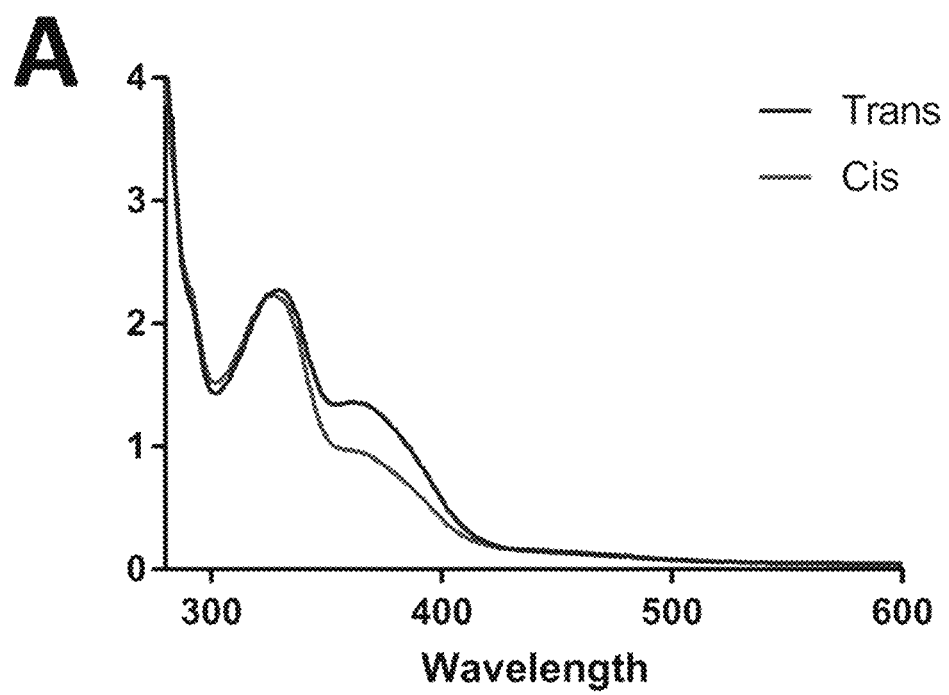
FIG. 3A shows UV-Vis absorption spectra of compound 4C-trans and cis configurations.
Figure 3B:
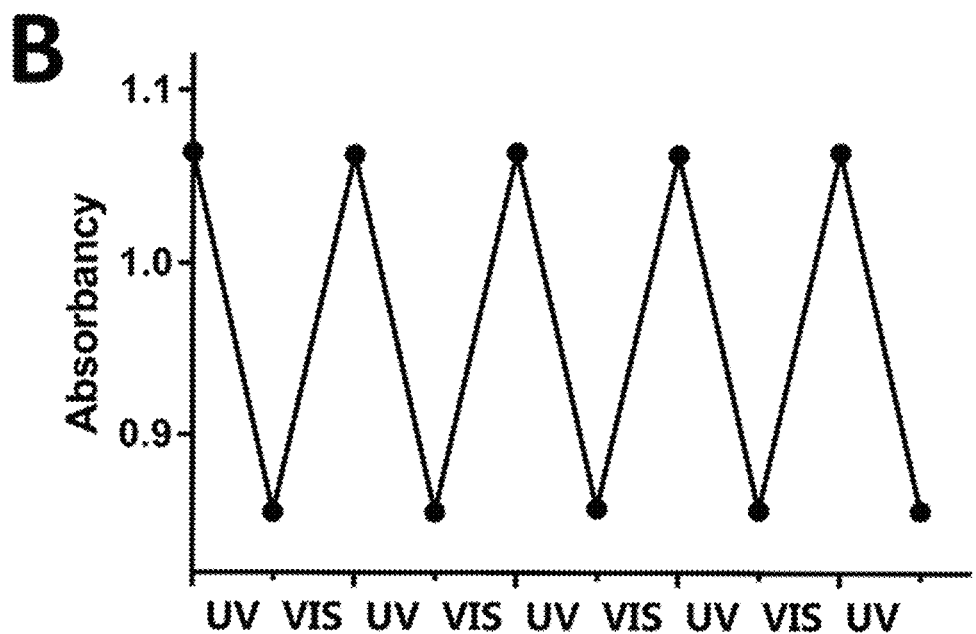
FIG. 3B shows detection of absorbency at $\lambda=361$ nm of compound 4C after UV-C irradiation in a periodic experiment.
Figure 3C:
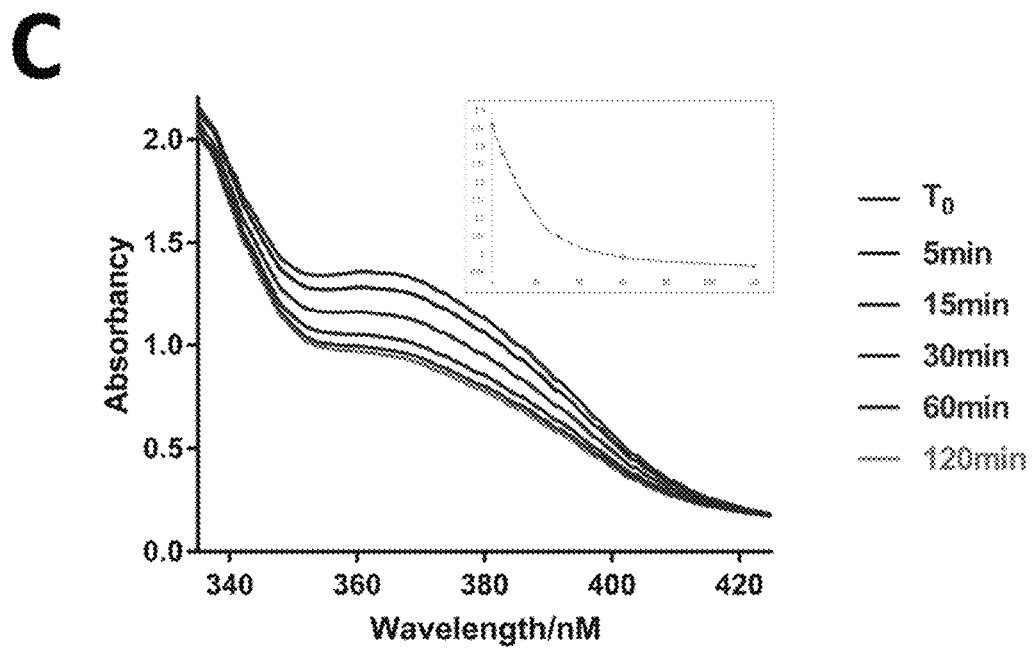
FIG. 3C shows change of the UV-Vis absorption spectrum of compound 4C-trans with time after UV irradiation.
Figure 3D:
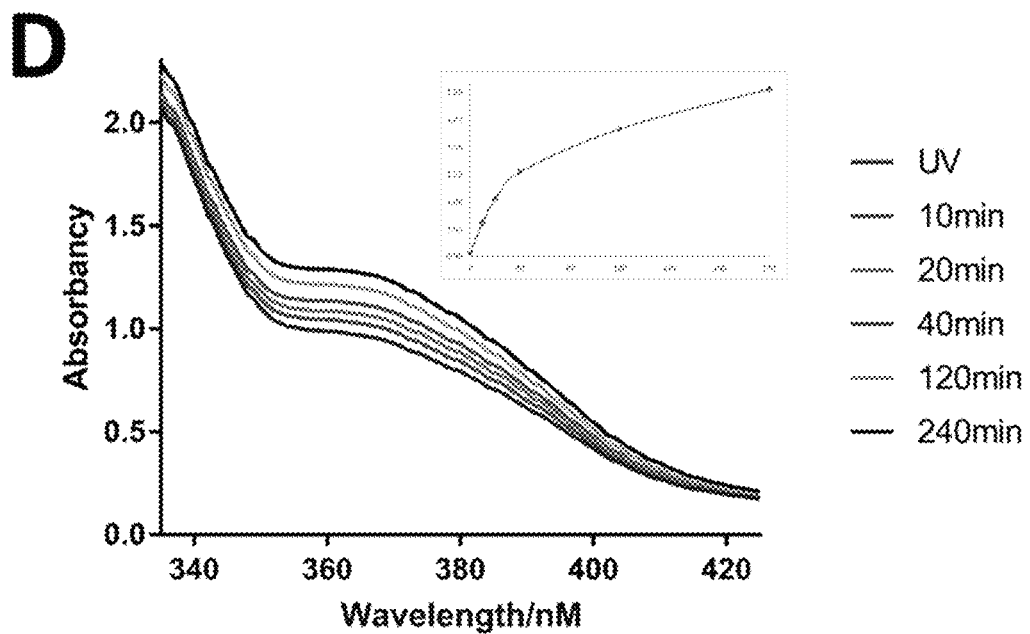
FIG. 3D shows change of UV-Vis absorption spectrum of compound 4C-cis with time after white light irradiation.

Studies have found that the compound 4C has good photo-isomerization activity. After the compound 4C was irradiated with 200-275 nM ultraviolet light (UV-C), the characteristic absorption peak of a trans-azophenyl group disappeared between 345-425 nm, indicating that the compound changed from a trans configuration to a cis configuration (FIG. 3A). Then, we explored the photodynamic characteristics of the compound 4C through UV-Vis absorption spectrum. The results showed that: the maximum absorption ($\lambda$max) of an azo group in the compound 4C-trans is at 361 nm. After UV irradiation, the peak at 361 nm gradually decreased, indicating that the compound gradually changed from the trans configuration to the cis configuration. An absorbency-time curve at 361 nm showed that the compound was almost completely transformed to the cis configuration after UV irradiation for 1 hour (FIG. 3B). The compound 4C in the cis configuration was gradually transformed into the trans configuration after white light irradiation (FIG. 3C). In addition, since the compound 4C is a T-type optical switch, the cis configuration underwent self-heating relaxation under dark conditions to transform into the trans configuration, and T½ was about 10 hours at 25° C. Then, we tested the reversibility of the photosensitive switch, and the results showed that the compound 4C was still relatively stable after being irradiated with ultraviolet light and white light in turn for 5 times.

Figure 4A:
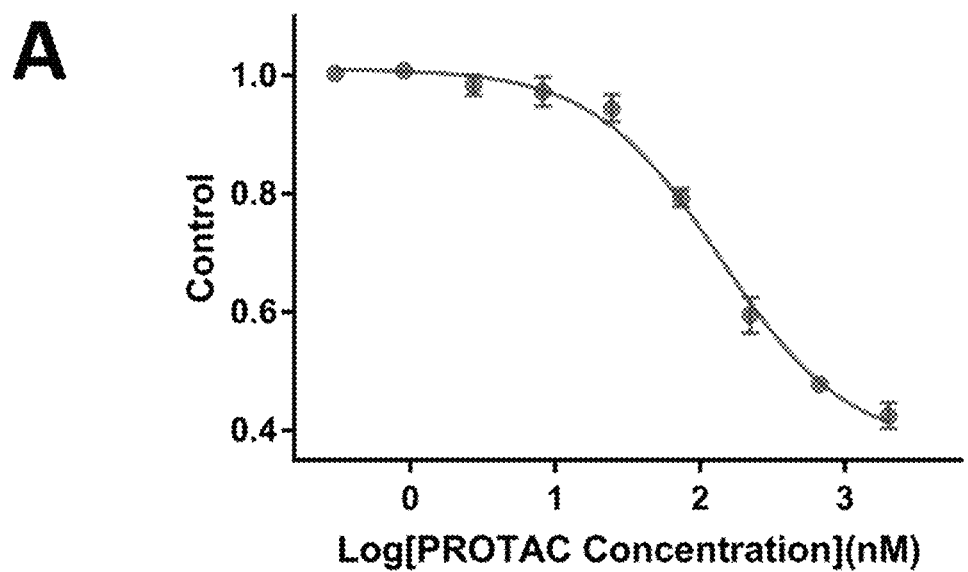
FIG. 4A shows determination of the anti-cell proliferation activity of compound 4C-trans on K562 cell lines.
Figure 4B:
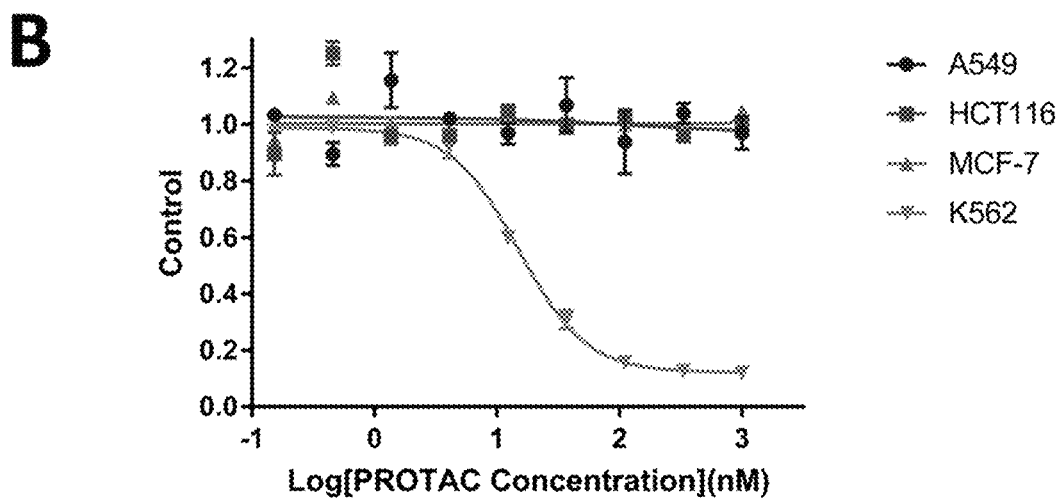
FIG. 4B shows determination of cell viability of A549, HCT116, MCF-7 and K562 cell lines under the action of compound 4C-trans.
Figure 4C:
FIG. 4C shows immunoblotting time-effect experiment of compound 4C-trans at a concentration of 250 nM.
Figure 4D:
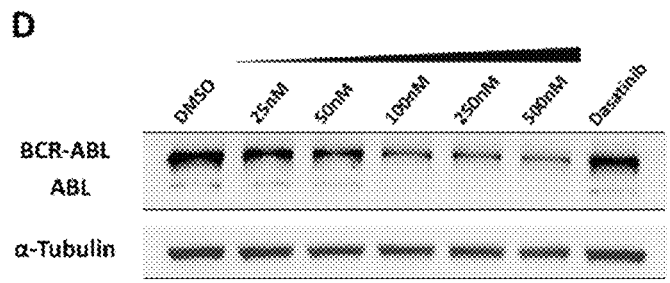
FIG. 4D shows immunoblotting dose-effect experiment of compound 4C-trans 24 hours after administration.

The researchers further evaluated the cell viability of the compound 4C. In an anti-K562 cell proliferation activity test, the median inhibitory concentration (IC50) of the compound 4C was 68 nM (FIG. 4A). In a cell viability test, the median effective concentration (EC50) of the compound 4C was 28 nM (FIG. 4B). In addition, the compound 4C hardly affects non-BCR-ABL dependent tumor cell lines, such as A549, HCT116, HEK293T and MCF-7 breast cancer (FIG. 4B). It can be seen that the compound 4C has good selectivity for the BCR-ABL dependent K562 cell line.

The operation method of the anti-K562 cell proliferation activity test is as follows:

100 μL of K562 cell suspension and 10 μL of test compounds of different concentrations were prepared in a 96-well plate. The culture plate was placed in an incubator for incubation for 48 hours (37° C., 5% $CO_2$). 10 μL of CCK-8 solution was added to each well. The culture plate was placed in an incubator for incubation for 1-4 hours. The absorbency was measured at 450 nm with a microplate reader.

Cytotoxicity (%)=[$A$ (with drug)–$A$ (blank)]/[$A$ (with 0 drug)–$A$ (blank)]×100, wherein:

$A$ (with drug): the absorbency of the wells containing cells, CCK-8 solution and drug solution $A$ (blank): the absorbency of wells containing medium and CCK-8 solution but no cells $A$ (with 0 drug): the absorbency of the wells containing cells and CCK-8 solution but no drug solution The operation method of the K562 cell viability test is as follows:

50 μL of K562, MCF-7, HCT116 and A549 cell suspensions were added to a 96-well plate and incubated for 12 hours. 10 μL of compound was added to the well and incubated for 48 hours. Operation was performed according to a CellTiter-Glo® luminescent cell viability assay kit (Promega). Nonlinear regression analysis data in GraphPad Prism 6 was used.

Figure 7:
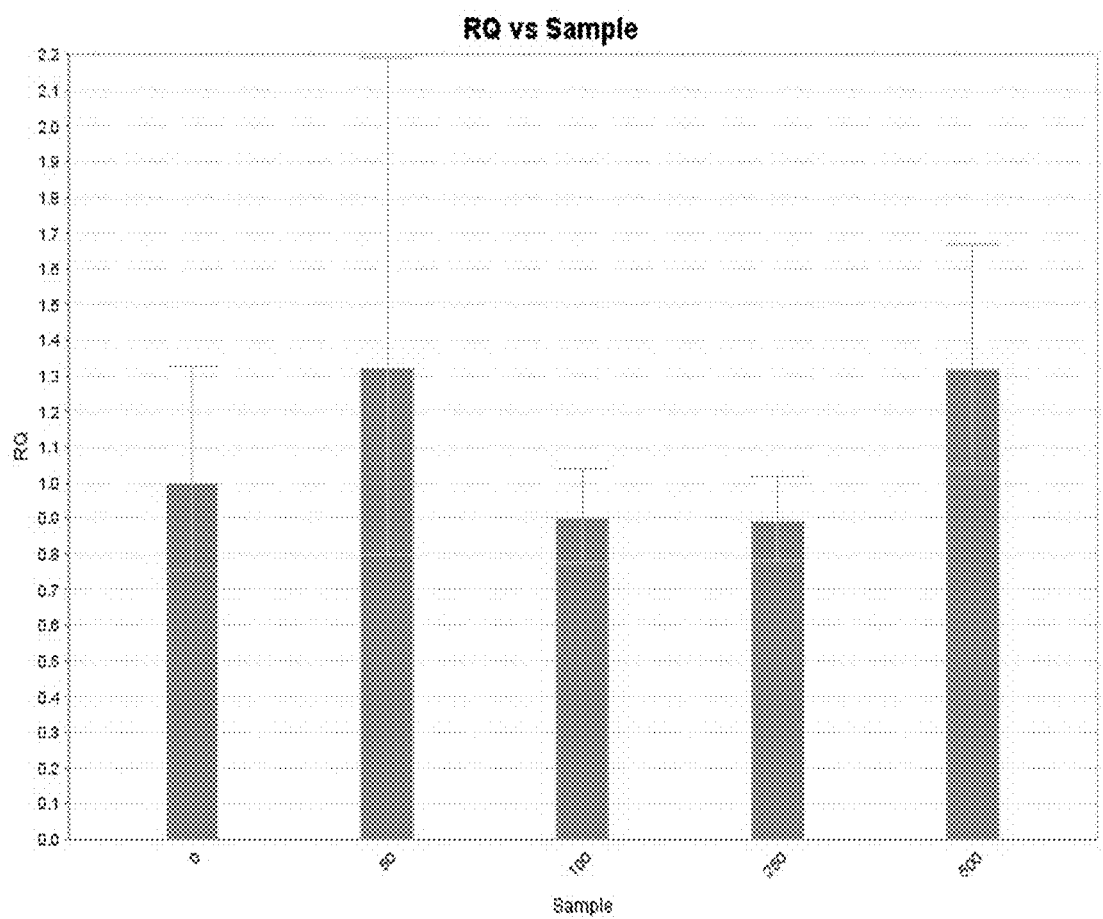
FIG. 7 shows the effect of different concentrations of compound 4C-trans on ABL gene expression.
Figure 8:
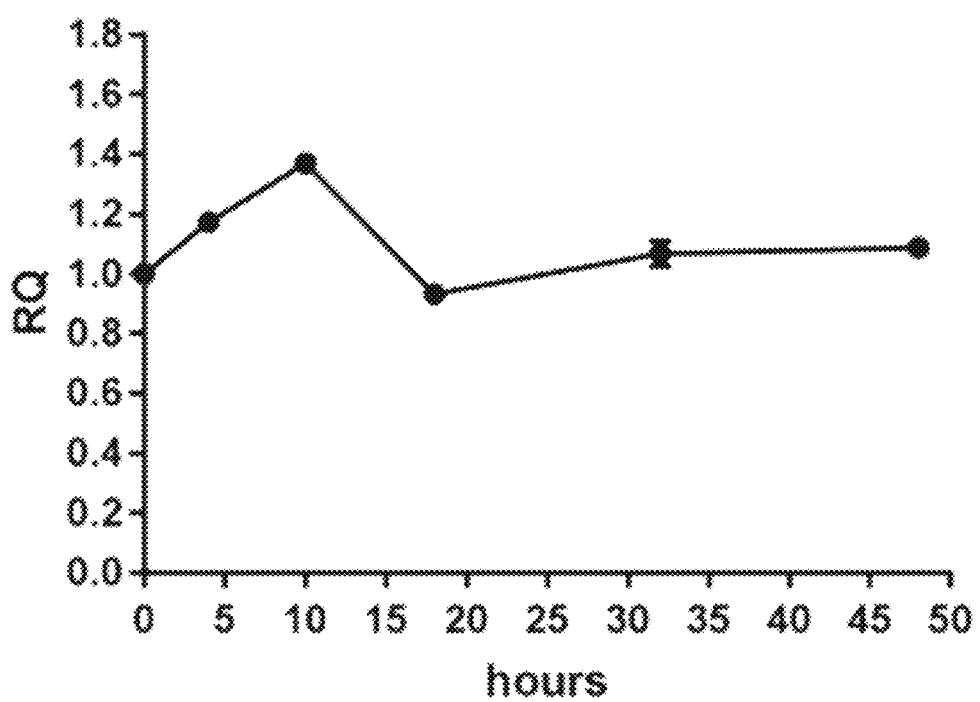
FIG. 8 is a curve showing change of the effect of compound 4C-trans at a concentration of 500 nM on ABL gene expression with time.

In order to test the degradation effect of the compound 4C on c-ABL and BCR-ABL proteins in K562 cells, the researchers performed an immunoblotting experiment. The time-effect experiment showed that ABL significantly reduced after 4 hours of incubation with the 250 nM compound 4C, BCR-ABL and c-ABL proteins were significantly degraded after 10 hours, ABL and BCR-ABL reached the maximum degradation after 32 hours, and after 48 hours, K562 cells showed obvious apoptosis. In order to exclude the possibility that the compound 4C affected the ABL gene to generate false positive expression, the researchers used RT-qPCR in K562 cells to study the expression of the ABL gene. The results are shown in FIG. 7 and FIG. 8. The dose-effect experiment showed that: compared with the control group, the mRNA level of the ABL gene in K562 cells treated with the compound 4C of different concentrations for 36 hours did not change significantly; and the time-effect experiment showed that the mRNA level of the ABL gene did not significantly decrease in K562 cells incubated with the compound 4C of 500 nm for 48 hours.

The operation method of the immunoblotting experiment is as follows:

A. Solutions and Reagents

The solutions were prepared with reverse osmosis deionized water (RODI) or equivalent water.

1*PBS: 50 ml of 20*PBS was added to 950 ml of dH2O and mixed.

1*TBS: 100 ml of 10*TBS was added to 900 ml of dH2O and mixed.

1*electrophoresis buffer: 100 ml of 10*electrophoresis buffer was added to 900 ml of dH2O and mixed.

1*transfer buffer: 100 ml of 10*transfer buffer was added to 100 ml of methanol+800 ml of dH2O, and mixed.

1*TBST: 100 ml of 10×TBST was added to 900 ml of dH2O and mixed.

Blocking buffer: 1*TBST containing 5% w/v skimmed milk powder.

Washing buffer: 1*BST.

Primary antibody dilution buffer: 1*TBST containing 5% skimmed milk powder; to prepare 20 ml of primary antibody dilution buffer, 1.0 g of skimmed milk powder was added to 20 ml of 1*TBST, and then mixed uniformly.

HRP conjugated secondary antibody: Anti-rabbit IgG, HRP-linked Antibody (#7074).

Detection reagent: SignalFire™ ECL Reagent (#6883).

B. Western Blot

Sample Preparation:

K562 cells after administration were incubated for 24 hours.

The medium was aspirated from the culture; the cells were washed with 1*PBS; and the cells were aspirated.

A weak RIPA lysate (100 μL) was added to lyse the cells for 40 min.

The sample was centrifuged at 13000 rpm, 4° C. for 15 min; 80 μl of supernatant was taken and added to 20 μl of loading buffer; the reaction solution was heated at 100° C. for 8 minutes; and the sample was placed on ice and cooled.

10 L of sample was loaded on 10% SDS-PAGE gel. The sample was transferred to a PVDF membrane by a wet process.

C. Membrane Blocking and Antibody Incubation

I. Membrane Blocking

A membrane was placed in 25 ml of blocking buffer and blocked at room temperature for 1 hour.

The membrane was washed three times with 15 ml of TBST for 5 minutes each time.

II. Primary Antibody Incubation

The membrane and the primary antibody (according to the appropriate dilution and diluent recommended in the product description) were placed in 10 ml of primary antibody dilution buffer, and incubated overnight at 4° C. and gently shaken from time to time.

The membrane was washed three times with 15 ml of TBST for 5 minutes each time.

Anti-rabbit IgG, HRP-linked Antibody (#7074, in a ratio of 1:2000) and anti-biotin, HRP-linked Antibody (#7075, in a ratio of 1:1000-1:3000) are diluted with 10 ml of blocking buffer to detect biotinylated protein standards. The membrane was incubated with the diluent, and gently shaken and incubated at room temperature for 1 hour.

The membrane was washed three times with 15 ml of TBST for 5 minutes each time.

Detection was continued (D part).

D. Protein Detection

Instruction:

The HRP (Antibody Conjugate) bound to the membrane was washed in TBST three times for 5 minutes.

A developer solution and the membrane were incubated together for 1 minute, the excess solution was discarded (the membrane remained moist) and the membrane was exposed.

The operation method of an RT-qPCR experiment is as follows:

According to the related gene information in the NCBI database, the coding sequences were selected, and primers were designed and synthesized by GenScript Biotechnology Corporation under entrustment. The sequences are as follows:

| Primer name | Sequence (5' to 3') | Base number | Primer's use | Purification method |
|---|---|---|---|---|
| BCR/ABLb3a2 sense | TCCACTCAGCCACTGGATTTAA (SEQ ID NO.: 1) | 22 | real time PCR | PAGE |
| antisense | TGAGGCTCAAAGTCAGATGCTACT (SEQ ID NO.: 2) | 24 | real time PCR | PAGE |

A K562 cell resuspension solution collected in a 1.5 mL centrifuge tube was centrifuged briefly. The culture supernatant was aspirated, an appropriate amount of Trizol reagent was added, the cells were lysed by pipetting repeatedly, and the lysate was allowed to stand at room temperature for 5 min. 0.2 time of chloroform by volume was added to the lysate, and the reaction solution was subjected to vortex treatment for 15 s and allowed to stand for 3 min at room temperature. The reaction solution was centrifuged at 12000 rpm and 4° C. for 15 min, the centrifuge tube was carefully taken out from a centrifuge, and the upper aqueous phase was aspirated and transferred into a new centrifuge tube. An equal volume of isopropanol was added and mixed uniformly, and the reaction solution was allowed to stand at room temperature for 10 min. The reaction solution was centrifuged at 12000 rpm and 4° C. for 15 min. At the time, a white RNA precipitate appeared at the bottom of the test tube. The supernatant was carefully discarded, 1 mL of 75% ethanol (0.1%, prepared with DEPC water) was added, and the reaction solution was inverted to mix evenly for 10 min. The reaction solution was centrifuged at 12000 rpm and 4° C. for 15 min. In order to dry the RNA precipitate in the air as soon as possible, 500 μL of absolute ethanol can be added to remove water. When the white nucleic acid just disappeared, an appropriate amount of 0.1% DEPC water was added for resuspension. After mixing uniformly, the purity and concentration of the extracted RNA sample were detected using a spectrophotometer. The ratio of A260/A280 of the RNA solution was the RNA purity, which is in a range of 1.8 to 2.1.

cDNA was prepared according to the following table. The bottom of the tube was flicked to mix the solution, and the solution was centrifuged briefly at 6000 rpm. Before adding the reverse transcriptase MMLV, the mixed solution was dry-bathed at 70° C. for 3 minutes. After being taken out, the mixed solution was bathed in ice water immediately until the temperatures inside and outside the tube were the same. Then 0.5 μl of reverse transcriptase was added, and the mixed solution was placed in a 37° C. water bath for 60 minutes. After being taken out, the mixed solution was dry-bathed immediately at 95° C. for 3 minutes to obtain the final reverse transcription solution, i.e. the cDNA solution, and the cDNA solution was stored at −80° C. for later use.

0.2 ml thin-walled PCR tubes were taken and numbered respectively. 2×qPCR TaqMix (12.5 μl, 10 μM), 0.5 μl each gene sense and anti-sense primer and 1 μl corresponding cDNA were added to each tube sequentially. One tube without template was used as a negative control. Water was added to each tube to 25 μl and mixed uniformly, and the mixed solutions were placed in an SLAN fluorescent quantitative PCR instrument. After pre-denaturation at 95° C. for 5 min, the mixed solutions were placed at 95° C. for 15 s→65° C. for 35 s (fluorescence detection), for 40 cycles.

| Serial number | Reactant | Dosage |
| --- | --- | --- |
| 1 | Reverse transcription buffer | 2 μl |
| 2 | Sense primer | 0.2 μl |
| 3 | Anti-sense primer | 0.2 μl |
| 4 | dNTP | 0.1 μl |
| 5 | Reverse transcriptase | 0.5 μl |
| 6 | DEPC water | 5 μl |
| 7 | RNA template | 2 μl |
| 8 | Total volume | 10 μl |

Figure 5B:
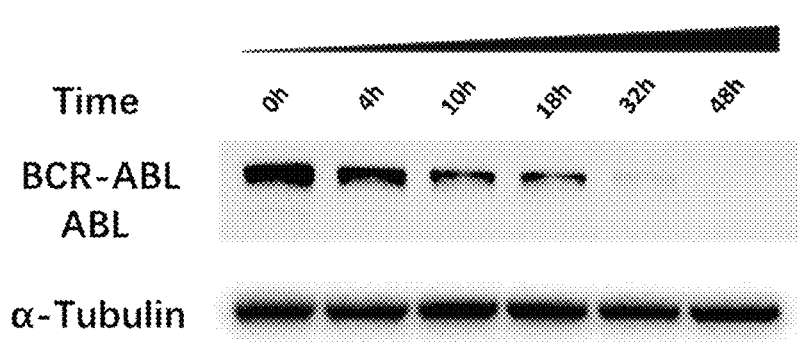
FIG. 5B shows immunoblotting-time effect experiment of compound 4C-trans at a concentration of 250 nM.
Figure 5C:
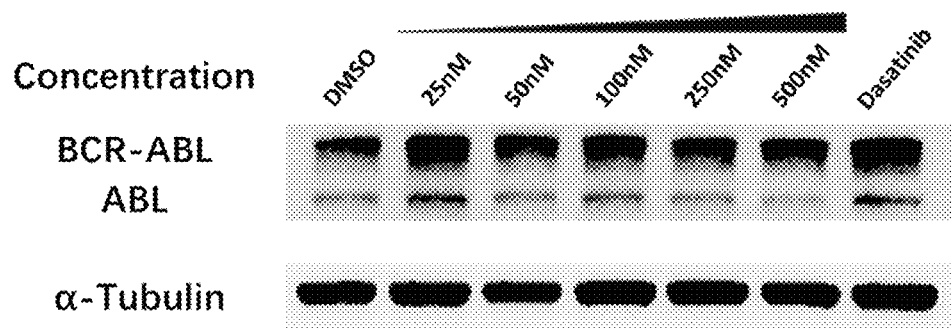
FIG. 5C shows immunoblotting-dose effect experiment of compound 4C-cis after 24 hours of incubation.
Figure 5D:
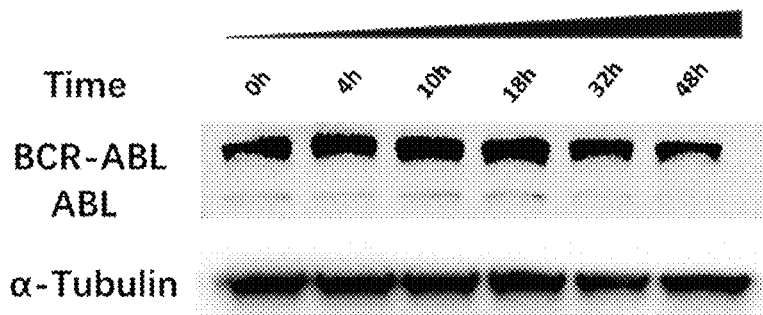
FIG. 5D shows immunoblotting-time effect experiment of compound 4C-cis at a concentration of 250 nM.

Next, we tested the difference in the activity of different configurations of compound 4C in degradation of ABL and BCR-ABL proteins. The results of immunoblotting showed that the 4C compound in the trans configuration could slightly degrade the BCR-ABL fusion protein at a concentration of 25 nM, and more than 80% of BCR-ABL and almost all ABL protein were degraded at a concentration of 500 nM (FIG. 5A). Under the same conditions, the 4C compound in the cis configuration did not significantly degrade the BCR-ABL protein at a concentration of 250 nM (FIG. 5C). A time-effect experiment showed that with the compound 4C in the trans configuration at the concentration of 250 nM, a slight decrease in BCR-ABL was observed after 4 hours, the BCR-ABL fusion protein was significantly reduced after 10 hours, and more than 90% of BCR-ABL fusion protein was degraded after 32 hours (FIG. 5B). Under the same conditions, the compound 4C in the cis configuration was not observed a significant reduction of BCR-ABL after 32 hours of incubation (FIG. 5D). The above results all prove that the trans and cis configurations of compound 4C are very different in degradation activity, and only the trans configuration can effectively degrade the BCR-ABL protein. The operation method of the immunoblotting experiment is the same as above.

Figure 6:
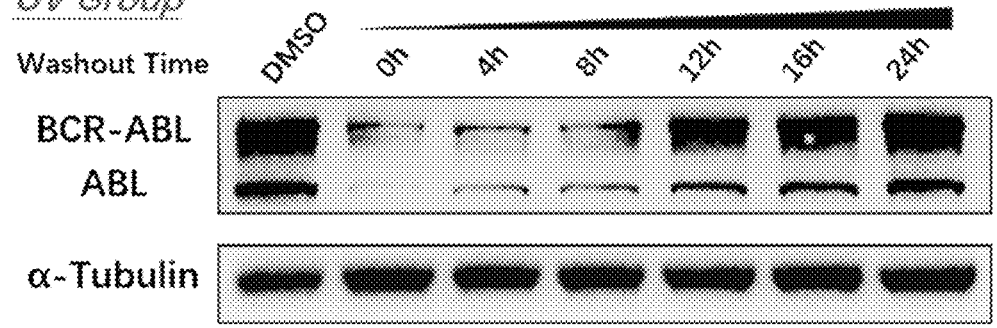
FIG. 6 shows change of the BCR-ABL protein concentration with time in K562 cells treated with compound 4C-trans in the dark (VIS group) and ultraviolet light (irradiated once every 4 hours) respectively.
Figure 6:
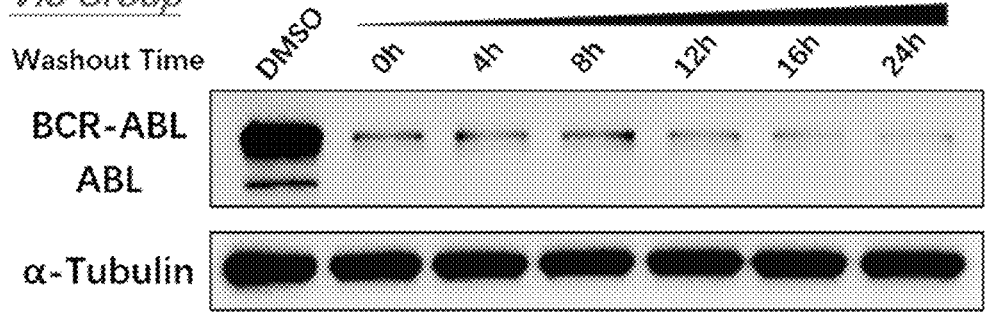

In order to simulate a light control process, the researchers treated K562 cells with the compound 4C-trans for 24 hours. Then the cells were transferred to fresh media and divided into 2 groups: one group was placed in a dark room (VIS group), and the other group was irradiated with UV after 0, 4, 8, 12, 16, and 24 hours of incubation to simulate the photo-isomerization process (UV group). The results showed that in the dark group, the BCR-ABL fusion protein remained at a low level, and ABL almost disappeared (FIG. 6—VIS), while in the UV group, the levels of ABL and BCR-ABL increased over time (FIG. 6—UV). These results all prove that the 4C compound changed in configuration after UV irradiation has lost the degradation activity, and through UV irradiation, we can stop the degradation process of PROTAC at any time.

The specific operation method for simulating light control is as follows:

The compound 4C-trans at a final concentration of 100 nM was added to K562 cells, and the cells were incubated at 37° C. for 24 hours. The medium was washed off, and the cells were washed 2 times with 1*PBS. Then the cells were transferred to fresh 1640 medium (10% FBS, 1*glutamine) for culture, and divided into two groups: one group was placed in a dark room, and the other group was irradiated with UV-C light for 30 min every 4 hours. The cells were collected after transfer and incubation for 0, 4, 8, 16, and 24 hours respectively, and post-treatment of the cells was the same as that of immunoblotting.

The function of the above examples is to specifically introduce the substantive content of the disclosure, but those skilled in the art should know that the protection scope of the disclosure should not be limited to these specific examples.

What is claimed is:
1. A compound of formula as shown as following:
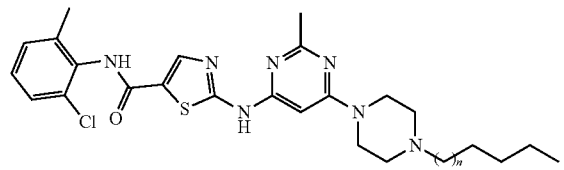
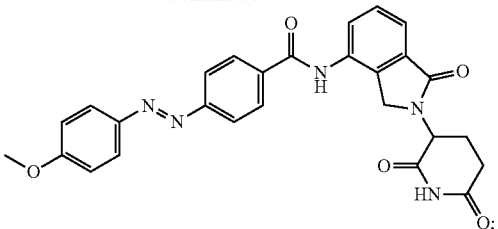
wherein n is an integer from 1 to −5.
2. The compound according to claim 1, wherein n=3.
3. A process for synthesizing the compound of claim 1 comprising chemical reactions as the following:
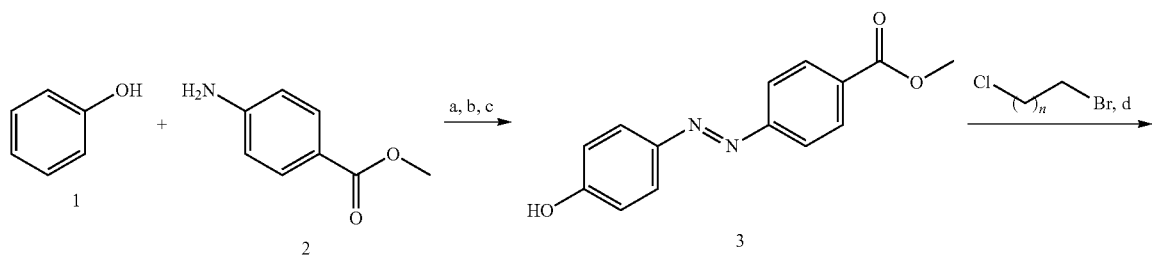
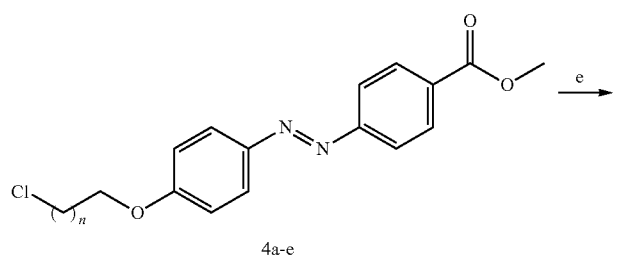
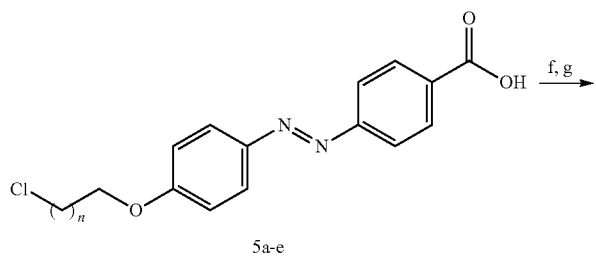
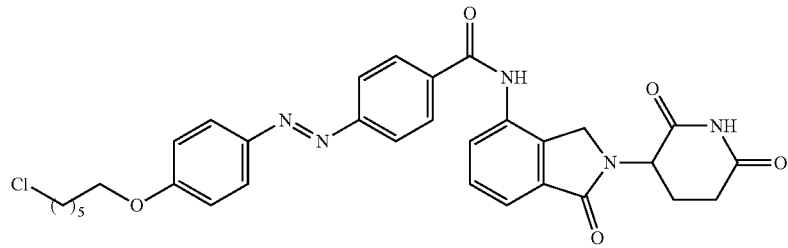

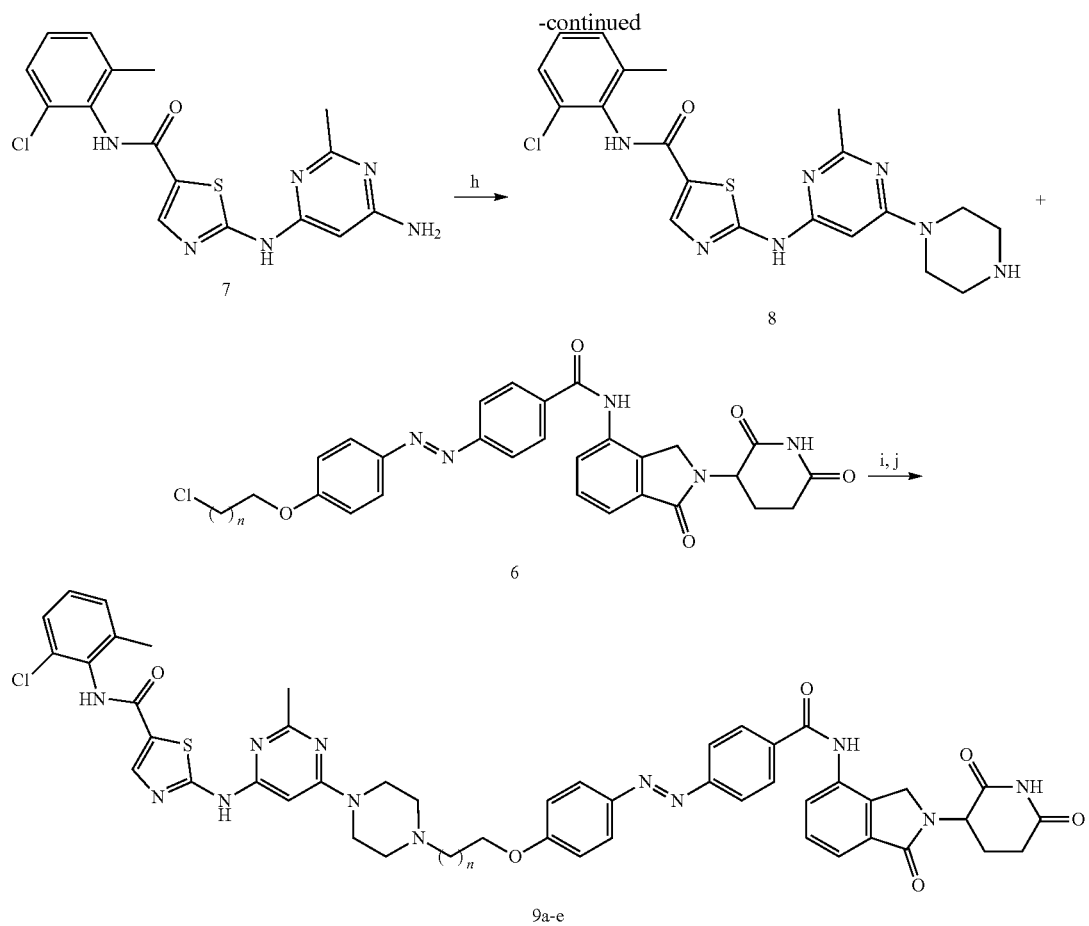

Reagents and conditions: a) HCl, NaNO$_2$/H$_2$O, 1 h; b) Cs$_2$CO$_3$, H$_2$O, rt, 3 h; c) AcOH, H$_2$O, pH = 4;
d) K$_2$CO$_3$, DMF; e) LiOH, THF:H$_2$O = 1:1, r.t., overnight; f) (COCl)$_2$, DMF(cat), DCM; g) Lenalidomide, DIEA, THF, rt., 8 h;
h) Piperazine, DIEA, Dioxane, reflux, 24 h; i) NaI, Acetone, reflux, 24 h; j) DIEA, DMF, 16 h;

4a, 5a, 6a, 9a: n = 1
4b, 5b, 6b, 9b: n = 2
4c, 5c, 6c, 9c: n = 3
4d, 5d, 6d, 9d: n = 4
4e, 5e, 6e, 9e: n = 5 wherein n is the integer between 1 and −5.

4. A method for treating a leukemia comprising a step of administrating an effective amount of the compound of claim 1 to a subject in need of treatment; wherein the leukemia is a BCR-ABL positive or/and a CRBN positive leukemia.

5. The method according to claim 4, wherein the compound degrades BCR-ABL and CRBN proteins.

* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: It is synthesized.

<400> SEQUENCE: 1
tccactcagc cactggatttt aa                    22

<210> SEQ ID NO 2
<211> LENGTH: 24
<212> TYPE: DNA
<213> ORGANISM: Artificial Sequence
<220> FEATURE:
<223> OTHER INFORMATION: It is synthesized.

<400> SEQUENCE: 2
tgaggctcaa agtcagatgc tact                   24